(12) United States Patent
Dorai et al.

(10) Patent No.: US 8,492,144 B2
(45) Date of Patent: Jul. 23, 2013

(54) METHODS FOR IMPROVING VIABILITY AND PRODUCTIVITY IN CELL CULTURE

(75) Inventors: Haimanti Dorai, Radnor, PA (US); Celia Ly, Malvern, PA (US); Tina M. Sauerwald McClain, Royersford, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 13/232,462

(22) Filed: Sep. 14, 2011

(65) Prior Publication Data

US 2012/0003735 A1 Jan. 5, 2012

Related U.S. Application Data

(62) Division of application No. 12/483,658, filed on Jun. 12, 2009, now abandoned.

(60) Provisional application No. 61/061,235, filed on Jun. 13, 2008.

(51) Int. Cl.
*C12N 5/071* (2010.01)
*C07K 14/00* (2006.01)

(52) U.S. Cl.
USPC ........ 435/358; 435/325; 530/350; 530/387.1; 536/23.2

(58) Field of Classification Search
USPC ..... 435/7.23, 69.3, 320.1, 325, 358; 530/350, 530/388.8, 387.1; 536/23.2
See application file for complete search history.

(56) References Cited

U.S. PATENT DOCUMENTS

| | | | |
|---|---|---|---|
| 6,890,716 B1 | 5/2005 | White et al. | |
| 2003/0064510 A1 | 4/2003 | Reff et al. | |
| 2005/0176075 A1 | 8/2005 | Jones et al. | |
| 2007/0092947 A1 | 4/2007 | Goldenberg et al. | |

FOREIGN PATENT DOCUMENTS

| WO | WO 2006/111387 A2 | 10/2006 |
|---|---|---|
| WO | WO2007/124106 A2 | 11/2007 |

OTHER PUBLICATIONS

Chen, et al., "Proteolytic Cleavage of the mdm2 Oncoprotein during Apoptosis," The Journal of Biological Chemistry, 272(36): 22966-22973 (1997).
Gu, et al., "Deregulation of Cdc2 kinase induces caspase-3 activation and apoptosis," Biochemical and Biophysical Research Communications, 302: 384-391 (2003).
Supplementary European Search Report dated Jun. 6, 2012 and sent to Applicants on Jun. 22, 2012.
Arden et al.,"*Inhibiting the Apoptosis Pathway Using MDM2 in Mammalian Cell Cultures*", Biotechnology. Bioengineering, 2007, pp. 601-614, vol. 97, No. 3, Wiley Periodicals, Inc.
Nivitchanyong et al., "*Anti-Apoptotic Genes Aven and E1B-19K Enhance Performance of BHK Cells Engineered to Express Recombinant Factor VIII in Batch and Low Perfusion Cell Culture*," Biotechnol. Bioeng. 2007, pp. 825-841, vol. 98, No. 4, Wiley Periodicals, Inc.
Sauerwald et al., "Inhibiting Apoptosis in Mammalian Cell Culture Using the Caspase Inhibitor XIAP and Deletion Mutants", Biotechnol. Bioeng., 2002 pp. 704-716, vol. 77, John Wiley & Sons, Inc.
Dorai et al., "*Expression of Anti-Apoptosis Genes Alters Lactate Metabolism of Chinese Hamster Ovary Cells in Culture*," Biotechnol. Bioeng., 2009, pp. 592-608, vol. 103, No. 3, Wiley Periodicals, Inc.
Goswami et al., "*Apoptosis in Batch Cultures of Chinese Hamster Ovary Cells*", Biotechnol. Bioeng., 1999, pp. 632-640, vol. 62, John Wiley & Sons, Inc.
Chiang and Sisk, "*Bcl-xL Mediates Increased Production of Humanized Monoclonal Antibodies in Chinese Hamster Ovary Cells*", Biotechnol. Bioeng., 2005, pp. 779-792, vol. 91, No. 7, Wiley Periodicals, Inc.
Figueroa et al, "*Comparison of Bcl-2 to a Bcl-2 Deletion Mutuant for Mammalian Cells Exposed to Culture Insults*", Biotechnol. Bioeng., 2001, pp. 211-222, vol. 73, No. 3, John Wiley & Sons, Inc.
Figueroa et al, "*A comparison of the properties of a Tcl-xL variant to the wild-type anti-apoptosis inhibitor in mammalian cell cultures*,"Metab. Eng., 2003, pp. 230-245, vol. 5, Science Direct.
Figueroa et al, "*Aven and Bcl-xL Enhance Protection Against Apoptosis for Mammalian Cells Exposed to Various Culture Conditions*,"Biotechnol. Bioeng., 2004, pp. 589-600, vol. 85, No. 6, Wiley Periodicals, Inc.
Mercille and Massie, "*Induction of Apoptosis in Nutrient-Deprived Cultures of Hybridoma and Myeloma Cells*", Biotechnol. Bioeng., 1994, pp. 1140-1154, vol. 44, No. 9, John Wiley & Sons, Inc.
Mercille and Massie, "Apoptosis-resistant NS/0 E1B-19K myelomas exhibit increased viability and Chimeric antibody productivity under cell cycle modulating conditions," Cytotechnology, 28(1-3): 189-203 (1998). Abstract only.
Arden and Betenbaugh, "*Life and Death in Mammalian Cell Culture: strategies for Apoptosis Inhibition*", Trends Biotechnol., 2004, pp. 174-180, vol. 22, No. 4, Science Direct.
Vives et al., "Metabolic engineering of apoptosis in cultured animal cells: implications for the biotechnology industry,"Metb. Eng. 2003, pp. 124-132 vol. 5, Elsevier Science, Science Direct.
Burteau et al, "*Fortification of a Protein-Free Cell Culture Medium with Plant Peptones Improves Cultivation and Productivity of an Interferon-y-Producing CHO Cell Line*," In Vitro Cell Dev. Biol. Anim., 2003, pp. 291-296, vol. 39, Society for In Vitro Biology.
Zhang and Robinson. "*Development of animal-free, protein-free and chemically-defined media for NS0 cell culture.*" Cytotechnology, 2005, pp. 59-74, vol. 48, Springer.
Mastrangelo et al, "*Overcoming apoptosis: new methods for improving protein-expression systems*", Trends Biotechnol., 1998, pp. 88-95, vol. 16, Elsevier Science, Ltd.
Meents et al, "*Impact of Coexpression and Coamplification of sICAM and Antiapoptosis Determinants bcl-2/bcl-xL on Productivity, Cell Survival, and Mitochondria Number in CHO-DG44 Grown in Suspension and Serum-Free Media*," Biotechnol. Bioeng., 2002, pp. 706-716, vol. 80, No. 6, Wiley Periodicals, Inc.
Tey et al, J. Biotechnol., "*Bcl-2 mediated suppression of apoptosis in myeloma NS0 cultures*," 2000, pp. 147-159, vol. 79, Elsevier.
Tey et al, "*Influence of Bcl-2 on Cell Death During the Cultivation of a Chinese Hamster Ovary Cell Line Expressing a Chimeric Antibody*", Biotechnol. Bioeng., 2000, pp. 31-48, vol. 68: No. 1, John Wiley & Sons, Inc.

(Continued)

Primary Examiner — Chih-Min Kam
(74) Attorney, Agent, or Firm — Kirk Baumeister

(57) ABSTRACT

Methods for increasing viability and production of secreted proteins in fed batch eukaryotic cell culture are disclosed.

4 Claims, 9 Drawing Sheets

OTHER PUBLICATIONS

Sauerwald et al., "*Study of Caspase Inhibitors for Limiting Death in Mammalian Cell Culture*," Biotechnol. Bioeng., 2003, pp. 329-340, vol. 81, No. 3, Wiley Periodicals, Inc.

Yasuda et al., "*Adenovirus E1B-19K/BCL-2 Interacting Protein BNIP3 Contains a BH3 Domain and a Mitochondrial Targeting Sequence*", J. Biol. Chem., 1998,:pp. 12415-12421, vol. 273, No. 20, The American Society for Biochemistry and Molecular Biology, Inc.

Bond et al, "*MDM2 is a Central Node in the p53 Pathway: 12 Years and Counting*", Current Cancer Drug Target, 2005, pp. 3-8, vol. 5, No. 1, Bentham Science Publishers, Ltd.

Arden et al, "*Cell Engineering Blocks Cell Stress and Improves Biotherapeutic Production*", Biotechnol. Bioeng., 2007, pp. 601-614, vol. 97, Bioprocessing journal.com.

Sauerwald et al, "*Apopsosis in Biotechnology: Its Role in Mammalian Cell Culture and Methods of Inhibition*,"Biopressing J., pp. 61-68, Summer, 2002, bioprocessingjournal.com.

Wilson et al, "*The Structure of an Antigenic Determinant in a Protein*,"Cell, 1984, pp. 767-778, vol. 37.

Gentz et al, "*Bioassay for trans-activation using purified human immunodeficiency virus tat-encoded protein: Trans-activation requires mRNA synthesis*," Proc. Natl Acad Sci., 1989, pp. 821-824, vol. 86, USA.

Gu et al., "*Deregulation of Cdc2 kinase induces caspase-3 activation and apoptosis*," Biochemical and Biophysical Research Communication, 2003, pp. 384-391, vol. 302.

GENBANK Accession Number AA152385 dated Jun. 10, 2008.

CNTO 328: Experiment CM7
Apoptosis: Growth Profile
Titer vs Time

SEQUENCE LISTING

```
<160> NUMBER OF SEQ ID NOS: 16

<210> SEQ ID NO 1
<211> LENGTH: 1476
<212> TYPE: DNA
<213> ORGANISM: Homo sapiens

<400> SEQUENCE: 1
atgtgcaata ccaacatgtc tgtacctact gatggtgctg taaccacctc acagattcca      60
gcttcggaac aagagaccct ggttagacca aagccattgc ttttgaagtt attaaagtct     120
gttggtgcac aaaaagacac ttatactatg aaagaggttc ttttttatct tggccagtat     180
attatgacta acgattata tgatgagaag caacaacata ttgtatattg ttcaaatgat     240
cttctaggag atttgtttgg cgtgccaagc ttctctgtga aagagcacag gaaaatatat     300
accatgatct acaggaactt ggtagtagtc aatcagcagg aatcatcgga ctcaggtaca     360
tctgtgagtg agaacaggtg tcaccttgaa ggtgggagtg atcaaaagga ccttgtacaa     420
gagcttcagg aagagaaacc ttcatcttca catttggttt ctagaccatc tacctcatct     480
agaaggagag caattagtga gacagaagaa aattcagatg aattatctgg tgaacgacaa     540
agaaaacgcc acaaatctga tagtatttcc ctttcctttg atgaaagcct ggctctgtgt     600
gtaataaggg agatatgttg tgaaagaagc agtagcagtg aatctacagg gacgccatcg     660
aatccggatc ttgatgctgg tgtaagtgaa cattcaggtg attggttgga tcaggattca     720
gtttcagatc agtttagtgt agaatttgaa gttgaatctc tcgactcaga agattatagc     780
cttagtgaag aaggacaaga actctcagat gaagatgatg aggtatatca agttactgtg     840
tatcaggcag gggagagtga tacagattca tttgaagaag atcctgaaat tccttagct      900 gactattgga aatgcacttc atgcaatgaa atgaatcccc ccttccatc acattgcaac     960 agatgttggg cccttcgtga gaattggctt cctgaagata aagggaaaga taaggggaa    1020 atctctgaga aagccaaact ggaaaactca acacaagctg aagagggctt tgatgttcct    1080
gattgtaaaa aaactatagt gaatgattcc agagagtcat gtgttgagga aaatgatgat    1140
aaaattacac aagcttcaca atcacaagaa agtgaagact attctcagcc atcaacttct    1200
agtagcatta tttatagcag ccaagaagat gtgaaagagt ttgaaaggga agaaacccaa    1260
gacaaagaag agagtgtgga atctagtttg ccccttaatg ccattgaacc ttgtgtgatt    1320
tgtcaaggtc gacctaaaaa tggttgcatt gtccatggca aaacaggaca tcttatggcc    1380
tgctttacat gtgcaaagaa gctaaagaaa aggaataagc cctgcccagt atgtagacaa    1440
ccaattcaaa tgattgtgct aacttatttc ccctag                              1476

<210> SEQ ID NO 2
<211> LENGTH: 491
<212> TYPE: PRT
<213> ORGANISM: Mus musculus
```

<400> SEQUENCE: 2

```
Met Cys Asn Thr Asn Met Ser Val Pro Thr Asp Gly Ala Val Thr Thr
 1               5                  10                  15
Ser Gln Ile Pro Ala Ser Glu Gln Glu Thr Leu Val Arg Pro Lys Pro
             20                  25                  30
Leu Leu Leu Lys Leu Leu Lys Ser Val Gly Ala Gln Lys Asp Thr Tyr
         35                  40                  45
Thr Met Lys Glu Val Leu Phe Tyr Leu Gly Gln Tyr Ile Met Thr Lys
 50                  55                  60
Arg Leu Tyr Asp Glu Lys Gln Gln His Ile Val Tyr Cys Ser Asn Asp
 65                  70                  75                  80
Leu Leu Gly Asp Leu Phe Gly Val Pro Ser Phe Ser Val Lys Glu His
                 85                  90                  95
Arg Lys Ile Tyr Thr Met Ile Tyr Arg Asn Leu Val Val Asn Gln
            100                 105                 110
Gln Glu Ser Ser Asp Ser Gly Thr Ser Val Ser Glu Asn Arg Cys His
            115                 120                 125
Leu Glu Gly Gly Ser Asp Gln Lys Asp Leu Val Gln Glu Leu Gln Glu
130                 135                 140
Glu Lys Pro Ser Ser Ser His Leu Val Ser Arg Pro Ser Thr Ser Ser
145                 150                 155                 160
Arg Arg Arg Ala Ile Ser Glu Thr Glu Glu Asn Ser Asp Glu Leu Ser
                165                 170                 175
Gly Glu Arg Gln Arg Lys Arg His Lys Ser Asp Ser Ile Ser Leu Ser
            180                 185                 190
Phe Asp Glu Ser Leu Ala Leu Cys Val Ile Arg Glu Ile Cys Cys Glu
            195                 200                 205
Arg Ser Ser Ser Ser Glu Ser Thr Gly Thr Pro Ser Asn Pro Asp Leu
210                 215                 220
Asp Ala Gly Val Ser Glu His Ser Gly Asp Trp Leu Asp Gln Asp Ser
225                 230                 235                 240
Val Ser Asp Gln Phe Ser Val Glu Phe Glu Val Glu Ser Leu Asp Ser
                245                 250                 255
Glu Asp Tyr Ser Leu Ser Glu Glu Gly Gln Glu Leu Ser Asp Glu Asp
            260                 265                 270
Asp Glu Val Tyr Gln Val Thr Val Tyr Gln Ala Gly Glu Ser Asp Thr
            275                 280                 285
Asp Ser Phe Glu Glu Asp Pro Glu Ile Ser Leu Ala Asp Tyr Trp Lys
290                 295                 300
Cys Thr Ser Cys Asn Glu Met Asn Pro Pro Leu Pro Ser His Cys Asn
305                 310                 315                 320
Arg Cys Trp Ala Leu Arg Glu Asn Trp Leu Pro Glu Asp Lys Gly Lys
                325                 330                 335
Asp Lys Gly Glu Ile Ser Glu Lys Ala Lys Leu Glu Asn Ser Thr Gln
            340                 345                 350
Ala Glu Glu Gly Phe Asp Val Pro Asp Cys Lys Lys Thr Ile Val Asn
            355                 360                 365
Asp Ser Arg Glu Ser Cys Val Glu Glu Asn Asp Asp Lys Ile Thr Gln
            370                 375                 380
Ala Ser Gln Ser Gln Glu Ser Glu Asp Tyr Ser Gln Pro Ser Thr Ser
385                 390                 395                 400
Ser Ser Ile Ile Tyr Ser Ser Gln Glu Asp Val Lys Glu Phe Glu Arg
                405                 410                 415
```

```
Glu Glu Thr Gln Asp Lys Glu Glu Ser Val Glu Ser Ser Leu Pro Leu
                420                 425                 430

Asn Ala Ile Glu Pro Cys Val Ile Cys Gln Gly Arg Pro Lys Asn Gly
            435                 440                 445

Cys Ile Val His Gly Lys Thr Gly His Leu Met Ala Cys Phe Thr Cys
450                 455                 460

Ala Lys Lys Leu Lys Lys Arg Asn Lys Pro Cys Pro Val Cys Arg Gln
465                 470                 475                 480

Pro Ile Gln Met Ile Val Leu Thr Tyr Phe Pro
                485                 490

<210> SEQ ID NO 3
<211> LENGTH: 1292
<212> TYPE: DNA
<213> ORGANISM: Artificial Sequence
<220> FEATURE:
<223> OTHER INFORMATION: Whereas the polynucleotide of SEQ ID NO:3
      encodes a Polypeptide comprising the mutant human MDM2D300A

<400> SEQUENCE: 3
atgactaaac gattatatga tgagaagcaa caacatattg tatattgttc aaatgatctt      60
ctaggagatt tgtttggcgt gccaagcttc tctgtgaaag agcacaggaa aatatatacc     120
atgatctaca ggaacttggt agtagtcaat cagcaggaat catcggactc aggtacatct     180
gtgagtgaga acaggtgtca ccttgaaggt gggagtgatc aaaaggacct tgtacaagag     240
cttcaggaag agaaaccttc atcttcacat ttggtttcta gaccatctac ctcatctaga     300
aggagagcaa ttagtgagac agaagaaaat tcagatgaat tatctggtga acgacaaaga     360
aaacgccaca aatctgatag tattttccctt tcctttgatg aaagcctggc tctgtgtgta     420
ataagggaga tatgttgtga agaagcagt agcagtgaat ctacagggac gccatcgaat     480
ccggatcttg atgctggtgt aagtgaacat tcaggtgatt ggttggatca ggattcagtt     540
tcagatcagt ttagtgtaga atttgaagtt gaatctctcg actcagaaga ttatagcctt     600
agtgaagaag gacaagaact ctcagatgaa gatgatgagg tatatcaagt tactgtgtat     660
caggcagggg agagtgatac agattcattt gaagaagatc ctgaaatttc cttagctgac     720
tattggaaat gcacttcatg caatgaaatg aatcccccccc ttccatcaca ttgcaacaga     780
tgttgggccc ttcgtgagaa ttggcttcct gaagataaag ggaaagataa aggggaaatc     840
tctgagaaag ccaaactgga aaactcaaca caagctgaag agggctttga tgtgccggct     900
tgtaaaaaac tatagtgaat gattccagag agtcatgtgt tgaggaaaat gatgataaaa     960
ttacacaagc ttcacaatca caagaaagtg aagactattc tcagccatca acttctagta    1020
gcattattta tagcagccaa gaagatgtga aagagtttga aagggaagaa acccaagaca    1080
aagaagagag tgtggaatct agtttgcccc ttaatgccat gaaccttgt gtgatttgtc    1140 aaggtcgacc taaaaatggt tgcattgtcc atggcaaaac aggacatctt atggcctgct    1200
ttacatgtgc aaagaagcta aagaaaagga ataagccctg cccagtatgt agacaaccaa    1260
ttcaaatgat tgtgctaact tatttcccct ag                                 1292

<210> SEQ ID NO 4
<211> LENGTH: 430
<212> TYPE: PRT
<213> ORGANISM: Artificial Sequence
<220> FEATURE:
<223> OTHER INFORMATION: Whereas SEQ ID NO:4 is a polypeptide comprising
      variant human MDM2 protein with a D300A substitution

<400> SEQUENCE: 4
```

```
Met Thr Lys Arg Leu Tyr Asp Glu Lys Gln His Ile Val Tyr Cys
 1               5                  10                 15

Ser Asn Asp Leu Leu Gly Asp Leu Phe Gly Val Pro Ser Phe Ser Val
            20                  25                  30

Lys Glu His Arg Lys Ile Tyr Thr Met Ile Tyr Arg Asn Leu Val Val
         35                  40                  45

Val Asn Gln Gln Glu Ser Ser Asp Ser Gly Thr Ser Val Ser Glu Asn
 50                  55                  60

Arg Cys His Leu Glu Gly Gly Ser Asp Gln Lys Asp Leu Val Gln Glu
 65                  70                  75                  80

Leu Gln Glu Glu Lys Pro Ser Ser His Leu Val Ser Arg Pro Ser
                 85                  90                  95

Thr Ser Ser Arg Arg Arg Ala Ile Ser Glu Thr Glu Glu Asn Ser Asp
            100                 105                 110

Glu Leu Ser Gly Glu Arg Gln Arg Lys Arg His Lys Ser Asp Ser Ile
         115                 120                 125

Ser Leu Ser Phe Asp Glu Ser Leu Ala Leu Cys Val Ile Arg Glu Ile
     130                 135                 140

Cys Cys Glu Arg Ser Ser Ser Glu Ser Thr Gly Thr Pro Ser Asn
145                 150                 155                 160

Pro Asp Leu Asp Ala Gly Val Ser Glu His Ser Gly Asp Trp Leu Asp
                 165                 170                 175

Gln Asp Ser Val Ser Asp Gln Phe Ser Val Glu Phe Glu Val Glu Ser
            180                 185                 190

Leu Asp Ser Glu Asp Tyr Ser Leu Ser Glu Glu Gly Gln Glu Leu Ser
         195                 200                 205

Asp Glu Asp Asp Glu Val Tyr Gln Val Thr Val Tyr Gln Ala Gly Glu
     210                 215                 220

Ser Asp Thr Asp Ser Phe Glu Glu Asp Pro Glu Ile Ser Leu Ala Asp
225                 230                 235                 240

Tyr Trp Lys Cys Thr Ser Cys Asn Glu Met Asn Pro Pro Leu Pro Ser
                 245                 250                 255

His Cys Asn Arg Cys Trp Ala Leu Arg Glu Asn Trp Leu Pro Glu Asp
            260                 265                 270

Lys Gly Lys Asp Lys Gly Glu Ile Ser Glu Lys Ala Lys Leu Glu Asn
         275                 280                 285

Ser Thr Gln Ala Glu Glu Gly Phe Asp Val Pro Ala Cys Lys Lys Thr
     290                 295                 300

Ile Val Asn Asp Ser Arg Glu Ser Cys Val Glu Glu Asn Asp Asp Lys
305                 310                 315                 320

Ile Thr Gln Ala Ser Gln Ser Gln Glu Ser Glu Asp Tyr Ser Gln Pro
                 325                 330                 335

Ser Thr Ser Ser Ser Ile Ile Tyr Ser Ser Gln Glu Asp Val Lys Glu
            340                 345                 350

Phe Glu Arg Glu Glu Thr Gln Asp Lys Glu Glu Ser Val Glu Ser Ser
         355                 360                 365

Leu Pro Leu Asn Ala Ile Glu Pro Cys Val Ile Cys Gln Gly Arg Pro
     370                 375                 380

Lys Asn Gly Cys Ile Val His Gly Lys Thr Gly His Leu Met Ala Cys
385                 390                 395                 400

Phe Thr Cys Ala Lys Lys Leu Lys Lys Arg Asn Lys Pro Cys Pro Val
                 405                 410                 415

Cys Arg Gln Pro Ile Gln Met Ile Val Leu Thr Tyr Phe Pro
```

<210> SEQ ID NO 5
<211> LENGTH: 660
<212> TYPE: DNA
<213> ORGANISM: Homo sapiens

<400> SEQUENCE: 5

```
atgtcgtccc acctagtcga gccgccgccg cccctgcaca acaacaacaa caactgcgag    60
gaaaatgagc agtctctgcc cccgccggcc ggcctcaaca gttcctgggt ggagctaccc   120
atgaacagca gcaatggcaa tgataatggc aatgggaaaa atgggggggct ggaacacgta   180
ccatcctcat cctccatcca caatggagac atggagaaga ttcttttgga tgcacaacat   240
gaatcaggac agagtagttc cagaggcagt tctcactgtg acagcccttc gccacaagaa   300
gatgggcaga tcatgtttga tgtggaaatg cacaccagca gggaccatag ctctcagtca   360
gaagaagaag ttgtagaagg agagaaggaa gtcgaggctt tgaagaaaag tgcggactgg   420
gtatcagact ggtccagtag acccgaaaac attccaccca aggagttcca cttcagacac   480
cctaaacgtt ctgtgtcttt aagcatgagg aaaagtggag ccatgaagaa agggggtatt   540
ttctccgcag aatttctgaa ggtgttcatt ccatctctct tcctttctca tgttttggct   600
ttggggctag gcatctatat tggaaagcga ctgagcacac cctctgccag cacctactga   660
```

<210> SEQ ID NO 6
<211> LENGTH: 219
<212> TYPE: PRT
<213> ORGANISM: Homo sapiens

<400> SEQUENCE: 6

Met Ser Ser His Leu Val Glu Pro Pro Pro Leu His Asn Asn Asn
1               5                  10                  15

Asn Asn Cys Glu Glu Asn Glu Gln Ser Leu Pro Pro Ala Gly Leu
            20                  25                  30

Asn Ser Ser Trp Val Glu Leu Pro Met Asn Ser Ser Asn Gly Asn Asp
        35                  40                  45

Asn Gly Asn Gly Lys Asn Gly Gly Leu Glu His Val Pro Ser Ser Ser
    50                  55                  60

Ser Ile His Asn Gly Asp Met Glu Lys Ile Leu Leu Asp Ala Gln His
65                  70                  75                  80

Glu Ser Gly Gln Ser Ser Arg Gly Ser Ser His Cys Asp Ser Pro
                85                  90                  95

Ser Pro Gln Glu Asp Gly Gln Ile Met Phe Asp Val Glu Met His Thr
            100                 105                 110

Ser Arg Asp His Ser Ser Gln Ser Glu Glu Val Val Glu Gly Glu
            115                 120                 125

Lys Glu Val Glu Ala Leu Lys Lys Ser Ala Asp Trp Val Ser Asp Trp
    130                 135                 140

Ser Ser Arg Pro Glu Asn Ile Pro Pro Lys Glu Phe His Phe Arg His
145                 150                 155                 160

Pro Lys Arg Ser Val Ser Leu Ser Met Arg Lys Ser Gly Ala Met Lys
                165                 170                 175

Lys Gly Gly Ile Phe Ser Ala Glu Phe Leu Lys Val Phe Ile Pro Ser
            180                 185                 190

Leu Phe Leu Ser His Val Leu Ala Leu Gly Leu Gly Ile Tyr Ile Gly
        195                 200                 205

Lys Arg Leu Ser Thr Pro Ser Ala Ser Thr Tyr

<210> SEQ ID NO 7
<211> LENGTH: 1089
<212> TYPE: DNA
<213> ORGANISM: Homo sapiens

<400> SEQUENCE: 7

```
atgcaggcgg agcgaggagc tcggggaggc cgtgggcggc ggccaggccg cggccggcct    60
ggcggagatc gccacagcga gcggcccgga ccgcagcgg cggtagccag aggcggcggc   120
ggaggcggcg gcggggacgg aggcggacgc cggggccgtg gccgtggccg gggcttccgc   180
ggcgctcgcg gaggccgagg aggaggaggc gccccgcgag gcagccgccg ggagccggga   240
ggctgggcg caggggccag cgcgccggtt gaagatgaca gcgatgcaga gacctatgga   300
gaagagaatg atgaacaggg aaattattct aaaagaaaga ttgtctctaa ctgggatcga   360
tatcaagata ttgaaaaaga ggtcaataat gaaagtggga agtcacagag gggaacagat   420
ttcagtgtcc tccttagctc tgcaggggac tcattctcac agttccggtt tgctgaggag   480
aaagaatggg atagtgaagc ttcttgtcca aaacagaatt cagcatttta tgtggatagt   540
gagttattgg ttcgagccct tcaagagctg cctctctgcc tccgactcaa cgttgctgcc   600
gaactggtcc agggtacagt tcctttagag gttcctcagg tgaaaccaaa agaactgat    660
gatggcaagg gattagggat gcagttaaag gggcccttgg ggcctggagg aagggggccc   720
atctttgagc tgaaatctgt ggctgctggc tgccctgtgt tgctgggcaa agacaaccca   780
agcccgggtc cttcaaggga ttctcagaaa cccacttccc cactgcagtc agcaggagac   840
catttggaag aagaactaga tctgttgctt aatttagatg cacctataaa agagggagat   900
aacatcttac cagatcagac gtctcaggac ctgaaatcca aggaagatgg ggaggtggtc   960
caagaggaag aagtttgtgc aaaccatct gtgactgaag aaaaaaacat ggaacctgag  1020
caaccaagta cctccaaaaa tgttaccgag gaagagctgg aagactggtt ggacagcatg  1080
atttcctaa                                                         1089
```

<210> SEQ ID NO 8
<211> LENGTH: 362
<212> TYPE: PRT
<213> ORGANISM: Homo sapiens

<400> SEQUENCE: 8

```
Met Gln Ala Glu Arg Gly Ala Arg Gly Arg Gly Arg Arg Pro Gly
 1               5                  10                  15

Arg Gly Arg Pro Gly Gly Asp Arg His Ser Glu Arg Pro Gly Ala Ala
                20                  25                  30

Ala Ala Val Ala Arg Gly Gly Gly Gly Gly Gly Asp Gly Gly
            35                  40                  45

Gly Arg Arg Gly Arg Gly Arg Gly Arg Gly Phe Arg Gly Ala Arg Gly
        50                  55                  60

Gly Arg Gly Gly Gly Gly Ala Pro Arg Gly Ser Arg Glu Pro Gly
65                  70                  75                  80

Gly Trp Gly Ala Gly Ala Ser Ala Pro Val Glu Asp Ser Asp Ala
                85                  90                  95

Glu Thr Tyr Gly Glu Glu Asn Asp Glu Gln Gly Asn Tyr Ser Lys Arg
            100                 105                 110

Lys Ile Val Ser Asn Trp Asp Arg Tyr Gln Asp Ile Glu Lys Glu Val
        115                 120                 125
```

```
Asn Asn Glu Ser Gly Glu Ser Gln Arg Gly Thr Asp Phe Ser Val Leu
    130                 135                 140
Leu Ser Ser Ala Gly Asp Ser Phe Ser Gln Phe Arg Phe Ala Glu Glu
145                 150                 155                 160
Lys Glu Trp Asp Ser Glu Ala Ser Cys Pro Lys Gln Asn Ser Ala Phe
                165                 170                 175
Tyr Val Asp Ser Glu Leu Leu Val Arg Ala Leu Gln Glu Leu Pro Leu
                180                 185                 190
Cys Leu Arg Leu Asn Val Ala Ala Glu Leu Val Gln Gly Thr Val Pro
            195                 200                 205
Leu Glu Val Pro Gln Val Lys Pro Lys Arg Thr Asp Asp Gly Lys Gly
    210                 215                 220
Leu Gly Met Gln Leu Lys Gly Pro Leu Gly Pro Gly Gly Arg Gly Pro
225                 230                 235                 240
Ile Phe Glu Leu Lys Ser Val Ala Ala Gly Cys Pro Val Leu Leu Gly
                245                 250                 255
Lys Asp Asn Pro Ser Pro Gly Pro Ser Arg Asp Ser Gln Lys Pro Thr
                260                 265                 270
Ser Pro Leu Gln Ser Ala Gly Asp His Leu Glu Glu Leu Asp Leu
            275                 280                 285
Leu Leu Asn Leu Asp Ala Pro Ile Lys Glu Gly Asp Asn Ile Leu Pro
    290                 295                 300
Asp Gln Thr Ser Gln Asp Leu Lys Ser Lys Glu Asp Gly Glu Val Val
305                 310                 315                 320
Gln Glu Glu Glu Val Cys Ala Lys Pro Ser Val Thr Glu Glu Lys Asn
                325                 330                 335
Met Glu Pro Glu Gln Pro Ser Thr Ser Lys Asn Val Thr Glu Glu Glu
                340                 345                 350
Leu Glu Asp Trp Leu Asp Ser Met Ile Ser
            355                 360

<210> SEQ ID NO 9
<211> LENGTH: 513
<212> TYPE: DNA
<213> ORGANISM: Homo sapiens

<400> SEQUENCE: 9
atgtctcaga gcaaccggga gctggtggtt gactttctct cctacaagct ttcccagaaa      60
ggatacagct ggagtcagtt tagtgatgtg aagagaaca ggactgaggc cccagaaggg     120
actgaatcgg agatggagac ccccagtgcc atcaatggca acccatcctg gcacctggca    180
gacagccccg cggtgaatgg agccactggc cacagcagca gtttggatgc ccggaggtg    240 atccccatgg cagcagtaaa gcaagcgctg agggaggcag gcgacgagtt tgaactgcgg    300
taccggcggg cattcagtga cctgacatcc cagctccaca tcaccccagg gacagcatat    360
cagagctttg aacaggatac ttttgtggaa ctctatggga caatgcagc agccgagagc    420 cgaaagggcc aggaacgctt caaccgctgg ttcctgacgg gcatgactgt ggccggcgtg    480
gttctgctgg gctcactctt cagtcggaaa tga                                 513

<210> SEQ ID NO 10
<211> LENGTH: 233
<212> TYPE: PRT
<213> ORGANISM: Homo sapiens

<400> SEQUENCE: 10

Met Ser Gln Ser Asn Arg Glu Leu Val Val Asp Phe Leu Ser Tyr Lys
```

```
                 1               5              10              15
Leu Ser Gln Lys Gly Tyr Ser Trp Ser Gln Phe Ser Asp Val Glu Glu
                    20              25              30

Asn Arg Thr Glu Ala Pro Glu Gly Thr Glu Ser Glu Met Glu Thr Pro
                35              40              45

Ser Ala Ile Asn Gly Asn Pro Ser Trp His Leu Ala Asp Ser Pro Ala
 50              55              60

Val Asn Gly Ala Thr Gly His Ser Ser Ser Leu Asp Ala Arg Glu Val
 65              70              75              80

Ile Pro Met Ala Ala Val Lys Gln Ala Leu Arg Glu Ala Gly Asp Glu
                    85              90              95

Phe Glu Leu Arg Tyr Arg Arg Ala Phe Ser Asp Leu Thr Ser Gln Leu
                100             105             110

His Ile Thr Pro Gly Thr Ala Tyr Gln Ser Phe Glu Gln Val Val Asn
                115             120             125

Glu Leu Phe Arg Asp Gly Val Asn Trp Gly Arg Ile Val Ala Phe Phe
            130             135             140

Ser Phe Gly Gly Ala Leu Cys Val Glu Ser Val Asp Lys Glu Met Gln
145             150             155             160

Val Leu Val Ser Arg Ile Ala Ala Trp Met Ala Thr Tyr Leu Asn Asp
                165             170             175

His Leu Glu Pro Trp Ile Gln Glu Asn Gly Gly Trp Asp Thr Phe Val
                180             185             190

Glu Leu Tyr Gly Asn Asn Ala Ala Ala Glu Ser Arg Lys Gly Gln Glu
            195             200             205

Arg Phe Asn Arg Trp Phe Leu Thr Gly Met Thr Val Ala Gly Val Val
            210             215             220

Leu Leu Gly Ser Leu Phe Ser Arg Lys
225             230

<210> SEQ ID NO 11
<211> LENGTH: 573
<212> TYPE: DNA
<213> ORGANISM: Homo sapiens

<400> SEQUENCE: 11
atggcgcacg ctgggagaac agggtacgat aaccgggaga tagtgatgaa gtacatccat      60
tataagctgt cgcagagggg ctacgagtgg gatgccgcgg ggcctgcgct cagcccggtg     120
ccacctgtgg tccacctgac cctccgccag gccggcgacg acttctcccg ccgctaccgc     180
cgcgacttcg ccgagatgtc cagccagctg cacctgacgc ccttcaccgc gcggggacgc     240
tttgccacgg tggtgaggga gctcttcagg acggggtga actgggggag gattgtggcc     300
ttctttgagt tcggtggggt catgtgtgtg gagagcgtca accgggagat gtcgcccctg     360
gtggacaaca tcgcccctgtg gatgactgag tacctgaacc ggcacctgca cctggatc     420 caggataacg gaggctggga tgcctttgtg aactgtacg gccccagcat gcggcctctg     480
tttgatttct cctggctgtc tctgaagact ctgctcagtt tggccctggt gggagcttgc     540 atcacccctgg gtgcctatct gagccacaag tga                                 573

<210> SEQ ID NO 12
<211> LENGTH: 190
<212> TYPE: PRT
<213> ORGANISM: Homo sapiens

<400> SEQUENCE: 12
```

```
Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Ala Gly Pro Ala Leu Ser Pro Val Pro Pro Val Val His Leu Thr Leu
        35                  40                  45

Arg Gln Ala Gly Asp Asp Phe Ser Arg Arg Tyr Arg Arg Asp Phe Ala
    50                  55                  60

Glu Met Ser Ser Gln Leu His Leu Thr Pro Phe Thr Ala Arg Gly Arg
65                  70                  75                  80

Phe Ala Thr Val Val Glu Glu Leu Phe Arg Asp Gly Val Asn Trp Gly
                85                  90                  95

Arg Ile Val Ala Phe Phe Glu Phe Gly Gly Val Met Cys Val Glu Ser
            100                 105                 110

Val Asn Arg Glu Met Ser Pro Leu Val Asp Asn Ile Ala Leu Trp Met
        115                 120                 125

Thr Glu Tyr Leu Asn Arg His Leu His Thr Trp Ile Gln Asp Asn Gly
    130                 135                 140

Gly Trp Asp Ala Phe Val Glu Leu Tyr Gly Pro Ser Met Arg Pro Leu
145                 150                 155                 160

Phe Asp Phe Ser Trp Leu Ser Leu Lys Thr Leu Leu Ser Leu Ala Leu
                165                 170                 175

Val Gly Ala Cys Ile Thr Leu Gly Ala Tyr Leu Ser His Lys
            180                 185                 190

<210> SEQ ID NO 13
<211> LENGTH: 1356
<212> TYPE: DNA
<213> ORGANISM: Homo sapiens

<400> SEQUENCE: 13
atgactttta acagttttga aggatctaaa acttgtgtac ctgcagacat caataaggaa      60
gaagaatttg tagaagagtt taatagatta aaaacttttg ctaattttcc aagtggtagt     120
cctgtttcag catcaacact ggcacgagca gggtttcttt atactggtga aggagatacc     180
gtgcggtgct ttagttgtca tgcagctgta gatagatggc aatatggaga ctcagcagtt     240
ggaagacaca ggaaagtatc cccaaattgc agatttatca acggctttta tcttgaaaat     300
agtgccacgc agtctacaaa ttctggtatc cagaatggtc agtacaaagt tgaaaactat     360
ctgggaagca gagatcattt tgccttagac aggccatctg agacacatgc agactatctt     420
ttgagaactg ggcaggttgt agatatatca gacaccatat acccgaggaa ccctgccatg     480
tatagtgaag aagctagatt aaagtccttt cagaactggc cagactatgc tcacctaacc     540
ccaagagagt tagcaagtgc tggactctac tacacaggta ttggtgacca agtgcagtgc     600
ttttgttgtg gtggaaaact gaaaaattgg gaaccttgtg atcgtgcctg gtcagaacac     660
aggcgacact ttcctaattg cttctttgtt ttgggccgga atcttaatat tcgaagtgaa     720
tctgatgctg tgagttctga taggaattttc ccaaattcaa caaatcttcc aagaaatcca     780
tccatggcag attatgaagc acggatcttt acttttggga catggatata ctcagttaac     840
aaggagcagc ttgcaagagc tggatttttat gcttaggtg aaggtgataa agtaaagtgc     900
tttcactgtg gagagggct aactgattgg aagcccagtg aagacccttg gaacaacat      960 gctaaatggt atccagggtg caaatatctg ttagaacaga agggacaaga atatataaac    1020
aatattcatt taactcattc acttgaggag tgtctggtaa gaactactga gaaaacacca    1080
```

```
tcactaacta gaagaattga tgataccatc ttccaaaatc ctatggtaca agaagctata   1140
cgaatggggt tcagtttcaa ggacattaag aaaataatgg aggaaaaaat tcagatatct   1200
gggagcaact ataaatcact tgaggttctg gttgcagatc tagtgaatgc tcagaaagac   1260
agtatgccag atgagtcaag tcagacttca ttacagaaag agattagtac tgaagagcag   1320
ctaaggcgcc tgcaagagga gaagcttatc gattga                             1356
```

<210> SEQ ID NO 14
<211> LENGTH: 451
<212> TYPE: PRT
<213> ORGANISM: Homo sapiens

<400> SEQUENCE: 14

```
Met Thr Phe Asn Ser Phe Glu Gly Ser Lys Thr Cys Val Pro Ala Asp
 1               5                  10                  15

Ile Asn Lys Glu Glu Glu Phe Val Glu Phe Asn Arg Leu Lys Thr
            20                  25                  30

Phe Ala Asn Phe Pro Ser Gly Ser Pro Val Ser Ala Ser Thr Leu Ala
        35                  40                  45

Arg Ala Gly Phe Leu Tyr Thr Gly Glu Gly Asp Thr Val Arg Cys Phe
    50                  55                  60

Ser Cys His Ala Ala Val Asp Arg Trp Gln Tyr Gly Asp Ser Ala Val
65                  70                  75                  80

Gly Arg His Arg Lys Val Ser Pro Asn Cys Arg Phe Ile Asn Gly Phe
                85                  90                  95

Tyr Leu Glu Asn Ser Ala Thr Gln Ser Thr Asn Ser Gly Ile Gln Asn
            100                 105                 110

Gly Gln Tyr Lys Val Glu Asn Tyr Leu Gly Ser Arg Asp His Phe Ala
        115                 120                 125

Leu Asp Arg Pro Ser Glu Thr His Ala Asp Tyr Leu Leu Arg Thr Gly
    130                 135                 140

Gln Val Val Asp Ile Ser Asp Thr Ile Tyr Pro Arg Asn Pro Ala Met
145                 150                 155                 160

Tyr Ser Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
            180                 185                 190

Gly Ile Gly Asp Gln Val Gln Cys Phe Cys Cys Gly Gly Lys Leu Lys
        195                 200                 205

Asn Trp Glu Pro Cys Asp Arg Ala Trp Ser Glu His Arg Arg His Phe
    210                 215                 220

Pro Asn Cys Phe Phe Val Leu Gly Arg Asn Leu Asn Ile Arg Ser Glu
225                 230                 235                 240

Ser Asp Ala Val Ser Ser Asp Arg Asn Phe Pro Asn Ser Thr Asn Leu
                245                 250                 255

Pro Arg Asn Pro Ser Met Ala Asp Tyr Glu Ala Arg Ile Phe Thr Phe
            260                 265                 270

Gly Thr Trp Ile Tyr Ser Val Asn Lys Glu Gln Leu Ala Arg Ala Gly
        275                 280                 285

Phe Tyr Ala Leu Gly Glu Gly Asp Lys Val Lys Cys Phe His Cys Gly
    290                 295                 300

Gly Gly Leu Thr Asp Trp Lys Pro Ser Glu Asp Pro Trp Glu Gln His
305                 310                 315                 320

Ala Lys Trp Tyr Pro Gly Cys Lys Tyr Leu Leu Glu Gln Lys Gly Gln
                325                 330                 335
```

```
Glu Tyr Ile Asn Asn Ile His Leu Thr His Ser Leu Glu Glu Cys Leu
            340                 345                 350
Val Arg Thr Thr Glu Lys Thr Pro Ser Leu Thr Arg Arg Ile Asp Asp
        355                 360                 365
Thr Ile Phe Gln Asn Pro Met Val Gln Glu Ala Ile Arg Met Gly Phe
    370                 375                 380
Ser Phe Lys Asp Ile Lys Lys Ile Met Glu Glu Lys Ile Gln Ile Ser
385                 390                 395                 400
Gly Ser Asn Tyr Lys Ser Leu Glu Val Leu Val Ala Asp Leu Val Asn
                405                 410                 415
Ala Gln Lys Asp Ser Met Pro Asp Glu Ser Ser Gln Thr Ser Leu Gln
                420                 425                 430
Lys Glu Ile Ser Thr Glu Glu Gln Leu Arg Arg Leu Gln Glu Glu Lys
                435                 440                 445
Leu Ile Asp
    450

<210> SEQ ID NO 15
<211> LENGTH: 45
<212> TYPE: DNA
<213> ORGANISM: Homo sapiens

<400> SEQUENCE: 15
gctgaagagg gctttgatgt gccggcttgt aaaaaaacta tagtg            45

<210> SEQ ID NO 16
<211> LENGTH: 7
<212> TYPE: PRT
<213> ORGANISM: Artificial Sequence
<220> FEATURE:
<223> OTHER INFORMATION: A putative caspase cleavage site identified in
      the wild type MDM2.

<400> SEQUENCE: 16

Ala Val Pro Asp Cys Lys Lys
1               5
```

METHODS FOR IMPROVING VIABILITY AND PRODUCTIVITY IN CELL CULTURE

This application is a divisional of U.S. application Ser. No. 12/483,658, filed 12 Jun. 2009, now abandoned, which claims priority to U.S. Provisional Application Ser. No. 61/061,235, filed 13 Jun. 2008, the entire contents of which is incorporated herein by reference in its entirety.

FIELD OF THE INVENTION

The present invention relates to methods of increasing viability and production of secreted proteins in fed batch eukaryotic cell culture.

BACKGROUND OF THE INVENTION

Mammalian cell culture is the system of choice for many recombinant protein production processes due to its ability to produce proteins with proper post-translational modifications. With increasing manufacturing demand, a strong motivation exists to improve process efficiency by increasing product yield. Attaining the grams per liter production levels of biotherapeutics in commercial production processes relies upon the optimization of both mammalian cell culture and engineering methods.

Inherent in current high density, protein-free mammalian cell cultures is the problem of cell death of which apoptosis can account for up to 80% in a typical fed-batch bioreactor, induced in response to stressors such as nutrient and growth factor deprivation, oxygen depletion, toxin accumulation, and shear stress (Goswami et al., Biotechnol. Bioeng. 62:632-640 (1999)). Apoptosis limits the maximum viable cell density, accelerates the onset of the death phase and potentially decreases heterologous protein yield (Chiang and Sisk, Biotechnol. Bioeng. 91:779-792 (2005); Figueroa et al., Biotechnol. Bioeng. 73:211-222 (2001), Metab. Eng. 5:230-245 (2003), Biotechnol Bioeng. 85:589-600 (2004); Mercille and Massie, Biotechnol. Bioeng. 44:1140-1154 (1994)).

Apoptosis is a result of a complex network of signaling pathways initiating from both inside and outside the cell, culminating in the activation of caspases that execute the final stages of cell death. Various methods of apoptosis prevention have been used to maintain cell viability during extended production runs in mammalian cell culture (Arden and Betenbaugh, Trends Biotechnol. 22:174-180 (2004); Vives et al., Metab. Eng. 5:124-132 (2003)). Altering the extracellular environment through media supplementation of growth factors, hydrolysates, and limiting nutrients has led to increased protein production and decreased apoptosis (Burteau et al., In Vitro Cell Dev. Biol. Anim. 39:291-296 (2003); Zhang and Robinson, Cytotechnology 48: 59-74 (2005)). Other researchers have turned to chemical and genetic strategies to inhibit the apoptotic signaling cascade from within the cell (Sauerwald et al., Biotechnol. Bioeng. 77:704-716 (2002), Biotechnol. Bioeng. 81:329-340 (2003)). Researchers have found that over-expression of genes found upregulated in cancer cells can prolong viability in cells grown in bioreactors by preventing apoptosis upstream of caspase activation (Goswami et al., supra; Mastrangelo et al., Trends Biotechnol. 16:88-95 (1998); Meents et al., Biotechnol. Bioeng. 80:706-716 (2002); Tey et al., J Biotechnol. 79:147-159 (2000) and Biotechnol. Bioeng. 68:31-43 (2000)).

The anti-apoptotic genes that function in the mitochondrial apoptotic pathway can be divided into three groups, namely 1) those that act early in the pathway, e.g., members of the Bcl-2 family of proteins; 2) those that act mid-pathway to disrupt or inhibit the apoptosome complex, e.g., Aven and 3) those that act late in the pathway, e.g., caspase inhibitors, XIAP. The functionality of the majority of these genes have been studied by over-expressing them in mammalian expression systems, and in some cases the effect of combined over-expression of two or more genes, each derived from a different part of the pathway has been determined. Examples include 1) the additive effect of Bcl-XL and a deletion mutant of XIAP (XIAP$\Delta$) in CHO cells (Figueroa et al., Metab. Eng. 5:230-245 (2003)); 2) E1B-19K and Aven in BHK cells (Nivitchanyong et al., Biotechnol. Bioeng. 98:825-841 (2007)) and 3) Bcl-XL, Aven and XIAP$\Delta$ (Sauerwald et al., Biotechnol. Bioeng. 81:329-340 (2003)).

One of the major activators of the apoptosis cascade is the protein p53. One mechanism by which p53 activates apoptosis is through up-regulation of a subset of pro-apoptosis proteins including BNIP3 (Yasuda et al., J. Biol. Chem. 273:12415-21 (1998)). Therefore, up-regulation of p53 may be one of the principal factors triggering apoptosis. p53 can be degraded in cells through ubiquitin mediated degradation pathway via MDM2 (murine double minute-2 gene) (Bond et al., Current Cancer Drug Target 5:3-8 (2005)). Thus, over-expression of MDM2 has the potential to lower p53 levels and by extension, inhibit apoptosis. Previously, it was shown that in the presence of stress signals, a CHO cell line over-expressing MDM2 could survive longer in culture compared to wild type CHO in batch culture (Arden et al., Biotechnol. Bioeng. 97:601-614 (2007)).

The various approaches described above to increase protein productivity have succeeded to varying degrees. Nevertheless, there is a continuous need to develop methods to increase protein production, especially in large-scale commercial production.

SUMMARY OF THE INVENTION

Figure 1A:
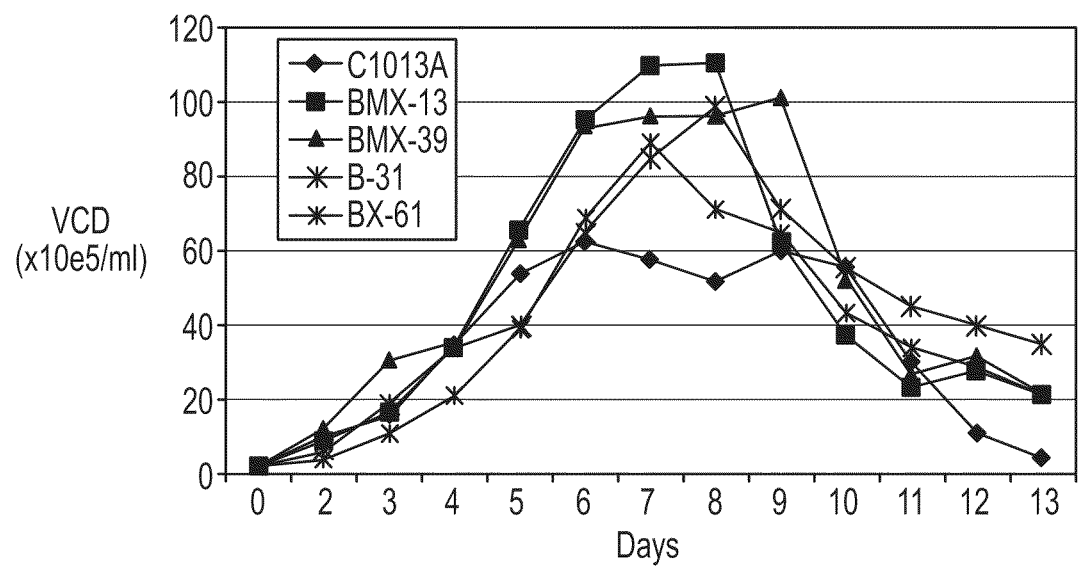
FIGS. 1A and 1B. A. Viable cell density (VCD) and B. integrated viable cell count (IVCC) of cell lines generated from co-transfection of Bcl-2$\Delta$, MDM-2 and XIAP$\Delta$.

One aspect of the invention is a method of increasing cell viability in a fed batch mammalian cell culture, comprising culturing a mammalian cell line over-expressing MDM2$^{D300A}$.

Another aspect of the invention is a method of increasing cell viability in a fed batch mammalian cell culture, comprising culturing a mammalian cell line over-expressing MDM2$^{D300A}$ and E1B19K.

Another aspect of the invention is a method of increasing production of a secreted protein in a Chinese Hamster Ovary (CHO) fed batch cell culture, comprising culturing a CHO cell line over-expressing MDM2$^{D300A}$ and one or more genes encoding the secreted protein.

Another aspect of the invention is a method of increasing production of a secreted protein in a Chinese Hamster Ovary (CHO) fed batch cell culture, comprising culturing a CHO cell line over-expressing MDM2$^{D300A}$ and E1B19K and one or more genes encoding the secreted protein.

Another aspect of the invention is a method of increasing production of a secreted protein in a Chinese Hamster Ovary (CHO) fed batch cell culture, comprising culturing a CHO cell line over-expressing MDM2$^{D300A}$ and E1B19K and one or more genes encoding the secreted protein.

Another aspect of the invention is an isolated polynucleotide encoding a polypeptide comprising the amino acid sequence shown in SEQ ID NO: 4.

Another aspect of the invention is an isolated polypeptide comprising a polypeptide having the sequence shown in SEQ ID NO: 4.

DETAILED DESCRIPTION OF THE INVENTION

All publications, including but not limited to patents and patent applications, cited in this specification are herein incorporated by reference as though fully set forth.

As used herein and in the claims, the singular forms "a," "and," and "the" include plural reference unless the context clearly dictates otherwise. Thus, for example, reference to "a polypeptide" is a reference to one or more polypeptides and includes equivalents thereof known to those skilled in the art.

The term MDM2 as used herein refers to human MDM2 (MDM2 p53 binding protein homolog) having a polypeptide sequence shown in GenBank accession number NP_002383 (SEQ ID NOs: 1 and 2).

The term E1B19K as used herein refers to human E1B19K protein, having a polypeptide sequence shown in GenBank accession number NP_004322 (SEQ ID NOs: 5 and 6).

The term "apoptotic$^R$ genes" as used herein refers to genes encoding proteins that, when over-expressed in a cell, confer increased resistance to cell death when compared to the untransfected cell. Exemplary apoptotic$^R$ genes are anti-apoptotic members of the Bcl-2 family, including Bcl-2, Bcl-XL, Blc-w or E1B19K, caspase inhibitors, for example the IAP family (inhibitors of apoptosis), including XIAP and XIAPΔ, and other proteins involved in cell cycle regulation, for example p27 and MDM2 (Arden et al., BioProcessing J. March/April 23-28 (2004); Sauerwald et al., Bioprocessing J. Summer 2002, 61-68 (2002); Arden et al., Biotechnol. Bioengineer. 97:601-614, (2007)). Cell death can be measured by methods well known in the art, for example by measuring Viable Cell Density (VCD) and percent (%) viability, and by calculating integrated viable cell density (IVCC). Activation of apoptosis can be measured by measuring caspase activity using well known methods.

The term "polypeptide" means a molecule that comprises at least two amino acid residues linked by a peptide bond to form a polypeptide. Small polypeptides of less than 50 amino acids may be referred to as "peptides". Polypeptides may also be referred as "proteins."

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

The term "complementary sequence" means a second isolated polynucleotide sequence that is antiparallel to a first isolated polynucleotide sequence and that comprises nucleotides complementary to the nucleotides in the first polynucleotide sequence. Typically, such "complementary sequences" are capable of forming a double-stranded polynucleotide molecule such as double-stranded DNA or double-stranded RNA when combined under appropriate conditions with the first isolated polynucleotide sequence.

The term "vector" means a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotides comprising a vector may be DNA or RNA molecules or hybrids of these.

The term "expression vector" means a vector that can be utilized in a biological system or a reconstituted biological system to direct the translation of a polypeptide encoded by a polynucleotide sequence present in the expression vector.

As used herein, the term "fed batch cell culture" means a cell culture process which is based on feeding of a growth limiting nutrient substrate to the culture. The fed batch strategy is typically used in bio-industrial processes to reach a high cell density in a bioreactor. Numerous strategies have been devised to improve viability and ultimately productivity of fed batch cell cultures. In the present invention, an alternative approach is described, whereby a combination of apoptotic$^R$ genes are over-expressed in a host cell. An uxpectedly high increase in the production of secreted proteins was demonstrated by cells engineered to over-express both MDM2 and E1B19K in the light of published results describing that expression of MDM-2 alone increased productivity by maximum of 2-fold (Arden et al., Biotechn. Bioengin. 97:601-614, 2007), and expression of E1B19K, although inhibiting apoptosis and improving cell yields, did not increase production of secreted proteins in a cell (WO2007/124106A2 of Betenbaugh). Further, cell lines generated during the studies described in the Examples below that over-expressed E1B19K only had less than optimal growth properties and low expression levels. Thus, the present invention demonstrated a significant benefit for production of secreted proteins in mammalian cells by co-expressing MDM2 and E1B19K.

The present invention also describes a non-naturally occurring mutant MDM2, which is useful in the methods of the invention.

One embodiment of the invention is a method if increasing cell viability in a fed batch mammalian cell culture, comprising culturing a mammalian cell line over-expressing one or more apoptotic$^R$ genes and evaluating cell viability.

The methods of the invention are useful for increasing viability in mammalian fed batch cell culture, such as Chinese Hamster Ovary (CHO) cell culture, myeloma or hybridoma cell culture. In particular, the methods of the invention are useful for increasing the integrated viable cell count (IVCC) of CHO cell cultures. The cell lines useful in the method of the invention express one or more apoptosis$^R$ genes. In particular, the genes encoding MDM2 (SEQ ID NOs 1 and 2), MDM2$^{D300A}$ (SEQ ID NOs 3 and 4), E1B19K (SEQ ID NOs: 5 and 6), Aven (SEQ ID NOs: 7 and 8), Bcl-LX (SEQ ID NO:s 9 and 10), Bcl-2Δ (SE ID NO: 11 and 12), and XIAPΔ (SEQ ID NOs: 13 and 14) can be used. Expression of the apoptosis$^R$ genes can be achieved by transfection techniques known to those skilled in the art. The cell lines generated are superior hosts for the development of production cell lines expressing proteins of interest such as peptides, peptide fusions, growth factors, hormones, antibodies, designed ankyrin repeat proteins (DARPins) and other polypeptides useful for therapeutic, diagnostic or research purposes. CHO cell lines useful in the method of the invention include CHO-K1 (Invitrogen, Carlsbad, Calif.) and CHOK1SV (Lonza Biologics, Slough, UK). Myeloma lines useful in the method of the invention include NS0 and Sp2/0.

In the present invention, the use of cell lines over-expressing apoptosis$^R$ genes allows these cell lines to reach IVCC values about two-fold higher than control cell, increase longevity of fed batch cultures up to 7 days, and improve production of secreted proteins by 2-7 fold. Such improved production is significant and can result in lower production costs for complex biologics and at the same time, generate product of superior quality due to the absence of cell lysis of the non-viable cells, as lysed cells release proteases that degrade product. Accordingly, these lines are superior hosts for the development of production cell lines expressing a protein or proteins of interest. For example, a CHO cell line over-expressing MDM2$^{D300A}$ reached 2-fold increased IVCC values and survived 7 days longer in culture when compared to control cell line.

Another embodiment of the invention is a method of increasing production of a secreted protein in a CHO fed batch cell culture, comprising culturing a CHO cell line over-expressing at least one apoptotic$^R$ genes and one or more genes encoding the secreted protein, and measuring the titer of the secreted protein. Particularly useful cell lines in the methods of the invention are CHO cell lines over-expressing MDM2 and E1B19K, and a cell line over-expressing MDM2$^{D300A}$ alone. Use of these cell lines in the methods of the invention resulted in 5- to 7-fold increased titers of secreted proteins in fed batch culture of up to 21 days.

Over-expression of proteins in a cell can be achieved by well known methods, either transiently or by stable expression (Davis et al., Basic Methods in Molecular Biology, 2$^{nd}$ ed., Appleton & Lange, Norwalk, Conn., 1994; Sambrook et al., Molecular Cloning: A Laboratory Manual, 3$^{rd}$ ed., Cold Spring Harbor Laboratory Press, Cold Spring Harbor, N.Y., 2001).

The present invention also provides isolated mutant MDM2 polynucleotides, vectors comprising these polynucleotides, isolated host cells, polypeptides obtainable from expression of these polynucleotides, methods for expressing the polypeptides of the invention, and methods of using the polynucleotides and polypeptides of the invention. The compositions and methods of the invention can be used for a variety of specific applications. The polynucleotides and vectors of the invention are useful because they encode mutant MDM2 polypeptides and can be used to express these polypeptides. The mutant MDM2 polypeptides are useful as they can be used to improve cell viability and increase production of secreted proteins in the cell when they are recombinantly overexpressed or introduced by other means into a host animal or tissue.

One aspect of the invention is an isolated polynucleotide comprising a polynucleotide having the sequence shown in SEQ ID NO: 3 or a complementary sequence thereof. The polynucleotide sequence shown in SEQ ID NO: 3 encodes a polypeptide comprising the mutant human MDM2$^{D300A}$. In the MDM2$^{D300A}$, a putative caspase cleavage site (AspVal-ProAspCysLysLys) (SEQ ID NO:16) identified in the wild type MDM2 was destroyed to confer MDM2 more resistant to degradation, and further increase MDM2 levels in the cell during culture. The polynucleotides of the invention may be produced by chemical synthesis such as solid phase polynucleotide synthesis on an automated polynucleotide synthesizer. Alternatively, the polynucleotides of the invention may be produced by other techniques such as PCR based duplication, vector based duplication, or restriction enzyme based DNA manipulation techniques. Techniques for producing or obtaining polynucleotides of a given known sequence are well known in the art.

The polynucleotides of the invention may also comprise at least one non-coding sequence, such as transcribed but not translated sequences, termination signals, ribosome binding sites, mRNA stabilizing sequences, introns and polyadenylation signals. The polynucleotide sequences may also comprise additional sequences encoding additional amino acids. These additional polynucleotide sequences may, for example, encode a marker or tag sequence such as a hexa-histidine peptide (Gentz et al., Proc. Natl. Acad. Sci. (USA) 86:821-284 (1989) or the HA peptide tag (Wilson et al., Cell 37:767-778 (1984)) which facilitate the purification of fused polypeptides.

Another embodiment of the invention is a vector comprising an isolated polynucleotide having a sequence shown in SEQ ID NO: 3. The vectors of the invention are useful for maintaining polynucleotides, duplicating polynucleotides, or driving expression of a polypeptide encoded by a vector of the invention in biological systems, including reconstituted biological systems. Vectors may be chromosomal-, episomal- and virus-derived such as vectors derived from bacterial plasmids, bacteriophages, transposons, yeast episomes, insertion elements, yeast chromosomal elements, baculoviruses, papova viruses such as SV40, vaccinia viruses, adenoviruses, fowl pox viruses, pseudorabies viruses, picornaviruses and retroviruses and vectors derived from combinations thereof, such as cosmids and phagemids.

The vectors of the invention can be formulated in microparticles, with adjuvants, lipid, buffer or other excipients as appropriate for a particular application.

In one embodiment of the invention the vector is an expression vector. Expression vectors typically comprise nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art. Nucleic acid sequence elements and parent vector sequences suitable for use in the expression of encoded polypeptides are also well known in the art. An exemplary plasmid-derived expression vector useful for expression of the polypeptides of the invention comprises an *E. coli* origin of replication, an aph(3')-1a kanamycin resistance gene, HCMV immediate early promoter with intron A, a synthetic polyA sequence and a bovine growth hormone terminator. Another exemplary plasmid derived expression vector comprises an *E. coli* origin of replication, an ant(4')-1a kanamycin resistance gene, Rous sarcoma virus long terminal repeat sequences, HCMV immediate early promoter and an SV40 late polyA sequence.

Another embodiment of the invention is an isolated host cell comprising a vector of the invention. Representative host cell examples include Archaea cells; bacterial cells such as *Streptococci, Staphylococci, Enterococci, E. coli, Streptomyces*, cyanobacteria, *B. subtilis* and *S. aureus*; fungal cells such as *Kluveromyces, Saccharomyces, Basidomycete, Candida albicans* or *Aspergillus*; insect cells such as *Drosophila* S2 and *Spodoptera* Sf9; animal cells such as CHO, COS, HeLa, C127, 3T3, BHK, 293, CV-1, Bowes melanoma and myeloma; and plant cells, such as gymnosperm or angiosperm cells. The host cells in the methods of the invention may be provided as individual cells, or populations of cells. Populations of cells may comprise an isolated or cultured population of cells or cells present in a matrix such as a tissue.

Introduction of a polynucleotide, such as a vector, into a host cell can be effected by methods well known to those skilled in the art (Davis et al., Basic Methods in Molecular Biology, 2nd ed., Appleton & Lange, Norwalk, Conn., 1994; Sambrook et al., Molecular Cloning: A Laboratory Manual, 3rd ed., Cold Spring Harbor Laboratory Press, Cold Spring Harbor, N.Y., 2001). These methods include calcium phosphate transfection, DEAE-Dextran mediated transfection, microinjection, cationic lipid-mediated transfection, electroporation, transduction, scrape loading, ballistic introduction and infection.

Another embodiment of the invention is an isolated polypeptide comprising a polypeptide having a sequence shown in SEQ ID NO: 4. SEQ ID NO: 4 is a polypeptide comprising variant human MDM2 protein with a D300A substitution. The polypeptides of the invention may be produced by chemical synthesis, such as solid phase peptide synthesis, on an automated peptide synthesizer. Alternatively, the polypeptides of the invention can be obtained from polynucleotides encoding these polypeptides by the use of cell-free expression systems such as reticulocyte lysate based expression systems, wheat germ extract based expression systems, and *Escherichia coli* extract based expression systems. The polypeptides of the invention can also be obtained by expression and isolation from cells harboring a nucleic acid sequence of the invention by techniques well known in the art, such as recombinant expression of easily isolated affinity labeled polypeptides. Those skilled in the art will recognize other techniques for obtaining the polypeptides of the invention. The polypeptides of the invention may comprise fusion polypeptides comprising a polypeptide of the invention fused with a second polypeptide. Such second polypeptides may be leader or secretory signal sequences, a pre- or pro- or prepro-protein sequence, as well as naturally occurring, or partially synthetic sequences derived in part from a naturally occurring sequence or an entirely synthetic sequence.

Another embodiment of the invention is a method for expressing a polypeptide comprising the steps of providing a host cell of the invention; culturing the host cell under conditions sufficient for the expression of at least one polypeptide comprising the sequence shown in SEQ ID NO: 4.

Host cells can be cultured under any conditions suitable for maintaining or propagating a given type of host cell and sufficient for expressing a polypeptide. Culture conditions, media, and related methods sufficient for the expression of polypeptides are well known in the art. For example, many mammalian cell types can be aerobically cultured at 37° C. using appropriately buffered DMEM media while bacterial, yeast and other cell types may be cultured at 37° C. under appropriate atmospheric conditions in LB media.

In the methods of the invention the expression of a polypeptide can be confirmed using a variety of different techniques well known in the art. For example, expression of $MDM2^{A300D}$ can be confirmed by Western blot or assaying ability of $MDM2^{A300D}$ to inhibit caspases.

The present invention will now be described with reference to the following specific, non-limiting examples.

EXAMPLES

In the following Examples, CHO cell lines over-expressing apoptotic$^R$ genes were analyzed in shake flask cultures for peak viable cell density, longevity, caspase 3/7 activation, and improved production of secreted proteins.

Materials and Methods:

Cell Culture:

CHOK1SV cell line (Lonza Biologics, Slough, UK), designated as the Control cell line C1013A, and CHOK1 (American Type Culture Collection, Manassas, USA), designated as the Control cell line C1835 were cultured in CD-CHO medium (Cat. No. 10743-011, Invitrogen, Carlsbad, Calif.), containing 30 mM Glucose and supplemented with 6 mM L-Glutamine (Invitrogen Cat. No. 10313-021). In some instances, another animal protein-free medium containing various concentrations including 60 mM glucose (defined as the high glucose medium) was used. Fetal Bovine serum was purchased from Hyclone Labs, Logan, Utah (Cat. No. SH30071.03). Cell cultures were monitored by a Cedex automated cell counting instrument (Innovatis, Germany). Integrated viable cell count (IVCC, cell-day/ml) was calculated using the following formula:

$$IVCC(d1)=[VCD(d0)+VCD(d1)]/2+VCD(d0),$$

where VCD=viable cell density

Expression Vectors:

Coding sequence of Bcl-2Δ (SEQ ID NO: 11) was cloned under the CMV promoter into the pCDNA™3.1(+) vector having Neo®. Coding sequence of Bcl-XL (SEQ ID NO: 9) was cloned under the CMV promoter into the pCDNA™3.1 (+) vector having Zeo®. Coding sequence of MDM2 (SEQ ID NO: 3) was cloned under the CMV promoter into the pCDNA™3.1(+) vector having Neo®. pBUDCE4.1 vector designed to constitutively express E1B-19K (EF-1a promoter), either alone or in conjunction with Aven (CMV promoter) has been described (Nivitchanyong et al., Biotechnol. Bioeng. 98:825-841 (2007)). The vector expressing XIAPΔ (CMV promoter) has been described (Sauerwald et al., Biotechnol. Bioeng. 77:704-716 (2002)). $MDM2^{D300A}$ expression vector was generated by in vitro mutagenesis from the MDM2 expression vector. A model antibody (Ab #1) expression vector was constructed by cloning a heavy and a light chain cDNA into a Glutamine Synthase (GS) expression vector (obtained from Lonza Biologics, Slough, UK, under a research license).

Generation of Apoptotic$^R$ Cell Lines:

An exponential culture of CHOK1SV cell line was transfected with various combinations of expression vectors as shown in Table 1. Transfectomas were selected using a combination of 400 µg/ml hygromycin, 400 µg/ml genticin, or 300 µg/ml Zeocin. About 200 resulting transfectomas were expanded into 24-well plate and caspase 3/7 activity determined by APO-ONE assay (Promega, Madison, Wis.). Two measurements were performed; a) early in growth phase (~day 3 post-seeding) following treatment with Staurosporine to induce apoptosis; and b) late in growth phase (~day 10 post-seeding), at which time, a subset of wild-type cells has progressed into apoptosis. Transfectomas that had reduced caspase 3/7 activities in both cases were further expanded and top two to four clones were subjected to shake-flask batch growth profile studies.

Promising cell lines were cryopreserved. Shake-flask cultures of selected lines were tested for reduced caspase 3 activity by FLOW, using fluorescent-labeled antibodies specific for caspase 3 (BD Bioscience; Cat. #68652X/550557). Selected cell lines were C-coded and submitted for cell banking. These cell lines underwent ten to 15 passage stability testing in the absence of antibiotics, which were used as selection agents. The cell lines generated are shown in Table 1. Expression of each transgene was confirmed in a select set of cell lines by Western blot.

TABLE 1

| Cell line | Over-expressed gene |
|---|---|
| B-31 | Bcl-2Δ |
| BX-61 | Bcl-2Δ and XIAPΔ |
| BMX-13 and BMX-39 | Bcl-2Δ, MDM2 and XIAPΔ |
| Bx-51 | Bcl-XL |
| BxMX-01, BxMX-11 and BxMX-25 | Bcl-XL, MDM2 and XIAPΔ |
| EM-15 and EM-70 | E1B19K and MDM2 |
| EAX-197 | E1B19K, AVEN and XIAPΔ |
| EA-167 | E1B19K and AVEN |
| C1013A | none |
| BM | MDM2 and Bcl-2Δ; |
| BxM | MDM2, Bcl-XL |
| EMX- | MDM2, E1B19K, XIAPΔ |

Shake-Flask Cultures of Apoptotic$^R$ Cell Lines:

Selected apoptotic$^R$ cell lines were cultured in batch mode in CD-CHO medium supplemented with 6 mM Glutamine and the requisite antibiotic selection agent(s). CD-CHO medium is formulated with 30 mM glucose. Additionally, select Ab-expressing cell lines were cultured in a custom formulated animal protein-free medium supplemented with 6 mM glutamine and 60 mM glucose.

Caspase 3/7 Activity Assay:

About $3\times10^5$ cells of each clone were seeded in one ml of growth medium in a 24-well plate. On day 4 (d4) post seeding, about $1\times10^5$ cells were transferred in triplicate to a 96 well plate. Staurosprine (2 μM fc) was added and the cells were incubated for 16 h before assaying for caspase3/7 activity by APO-ONE kit (BD Labs). The procedure was repeated on d10, except that Staurosporine was omitted. The clones that had significantly lower caspase3/7 activity on both days were expanded into shake flasks. The apoptotic$^R$ nature of the selected clones was confirmed by flow cytometry analysis (see below).

Analysis of Apoptotic$^R$ Clones by Flow Cytometry:

About $1\times10^6$ cells from exponential cultures were withdrawn from each shake flask into 24 well plates, incubated with Staurosporine (2 μM fc) for 16 h, harvested and washed once in PBS. The cells were then incubated with CytoPerm (Cat. No. 2075KK, BD BioScience) to fix and permeablized them. Following a PBS wash, cells were incubated with FITC-labeled anti-caspase3 (Cat. No. 68654, BD BioScience) antibody before subjecting them to analysis by flow cytometry.

Example 1

Effect of MDM2 on Bcl-2Δ Expressing Cell Lines

Figure 1B:
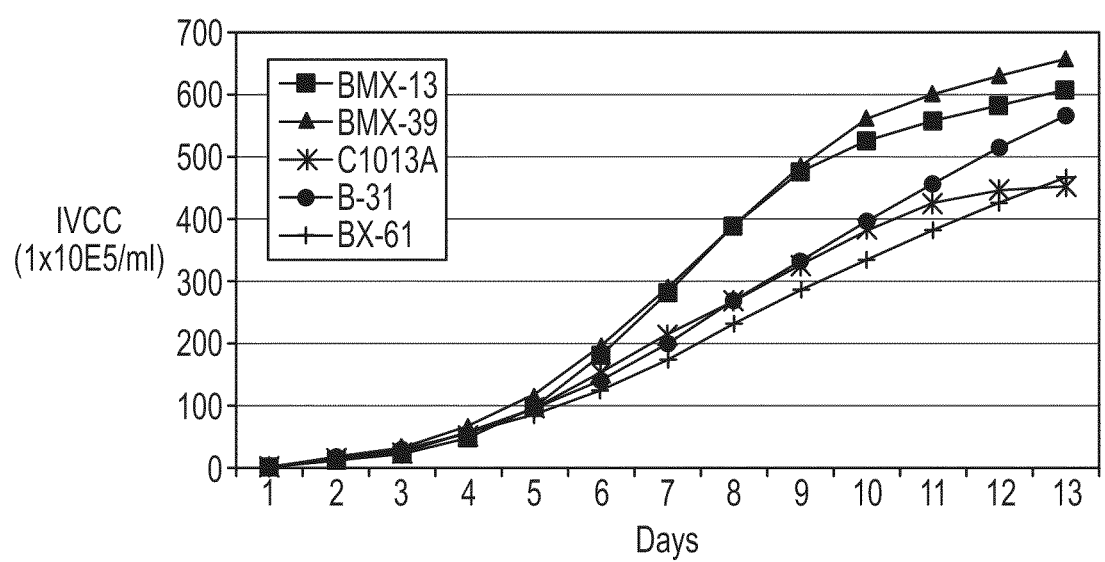

Growth profiles (SF/Batch) of BMX-13 and BMX-39, expressing Bcl-2Δ, MDM2 and XIAPΔ, as well as double transfected cell line BX-61 expressing Bcl-2Δ and XIAPΔ, B-31 expressing Bcl-2Δ alone, and the control C1013A were analyzed. The peak viable cell count (VCD) of the control cell line reached 6×10e6 cellsm/ml whereas those of BMX clones reached about 11×10e6 cells/ml. Cell lines expressing Bcl-2Δ and/or XIAPΔ had intermediate VCD (FIG. 1A). BMX clones had higher integrated viable cell count (IVCC) compared to B-31 or BX-61. BMX-39 had a 44% increase in IVCC over control as compared to 23% for B-31. XIAPΔ had no incremental effect on IVCC when used in conjunction with Bcl-2Δ (FIG. 1B). High IVCC correlates with high viability of cells in the long term culture in a bioreactor, resulting in increased product yields. Further, biopharmaceuticals generated from a production cell line derived from an apoptotic$^R$ host cell line may be of superior quality. Cell lines BMX-13 and BMX-39 demonstrated caspase 3/7 downregulation by 10-fold and 16-fold, respectively when compared to the control C1013A, confirming anti-apoptotic effect of the genes in the CHO cell line. B-31 and BX-61 had had 12- and 6-fold downregulation of caspases.

Example 2

Effect of MDM2 on Bcl-XL Expressing Cell Lines

Figure 2A:
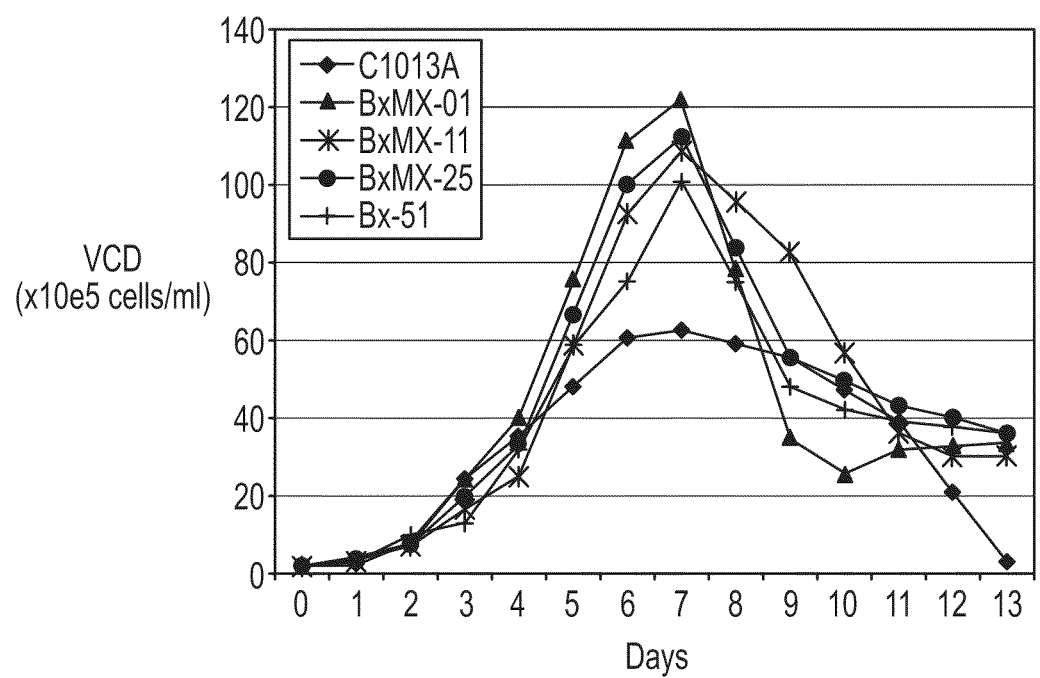
FIGS. 2A and 2B. A. Viable cell density (VCD) and B. integrated viable cell count (IVCC) of cell lines generated from co-transfection of Bcl-XL, MDM-2 and XIAP$\Delta$.
Figure 2B:
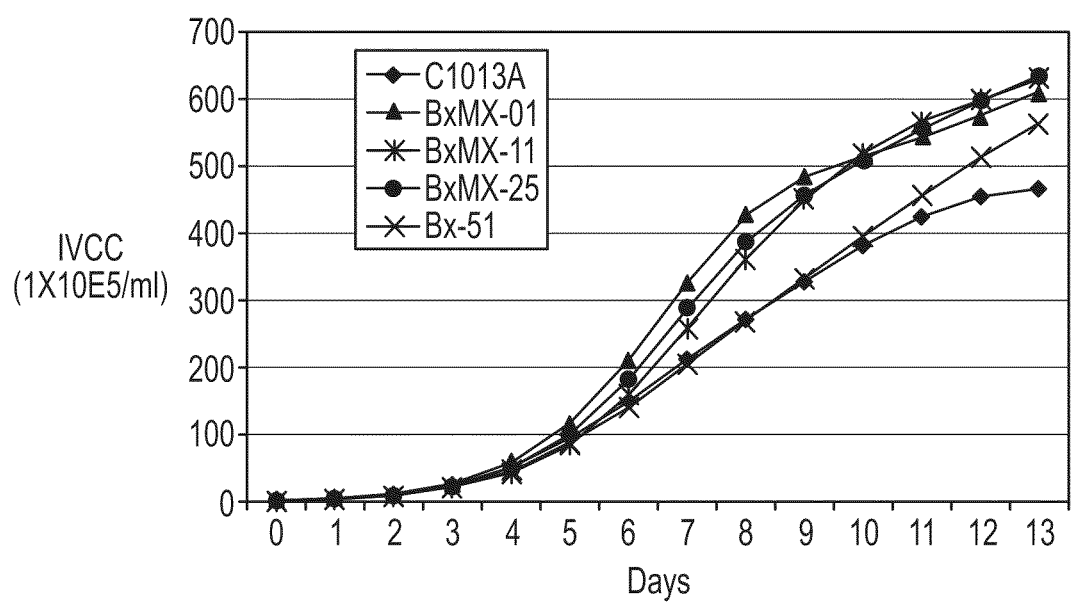

Growth profiles of triple transfected BxMX-01, BxMX11 and BxMX-25, expressing Bcl-XL, MDM2 and XIAPΔ in comparison to Bx-51 expressing Bcl-XL alone as well as the control cell line C1013 were evaluated. The peak viable cell count (VCD) of control cell line reached 6×10e6 cells/ml whereas those of BxMX clones reached about 12×10e6 cells/ml (FIG. 2A). Cell lines expressing Bcl-XL only had intermediate VCD. For example, the peak VCD of cell line Bx-51 was 10×10e6 cells/ml. BxMX clones had higher IVCC compared to Bx-51 with 34% increase in IVCC over control as compared to 18% for Bx-51 (FIG. 2B). Co-transfection of Bcl-XL and MDM2 only (without XIAPΔ) failed to generate cell lines with higher VCD or extended longevity (data not shown). Thus, XIAPΔ and MDM2 are likely to function synergistically towards achieving the high IVCC observed in BxMX-01, BxMX-11 and BxMX-25 cell lines. Caspase 3/7 activity was down-regulated 7-, 5-, and 8-fold in BxMX-01, BxMx-11 and BxMX-25, respectively, as compared to control C1013A.

Example 3

Effect of MDM2 on E1B19K Expressing Cell Lines

Figure 3:
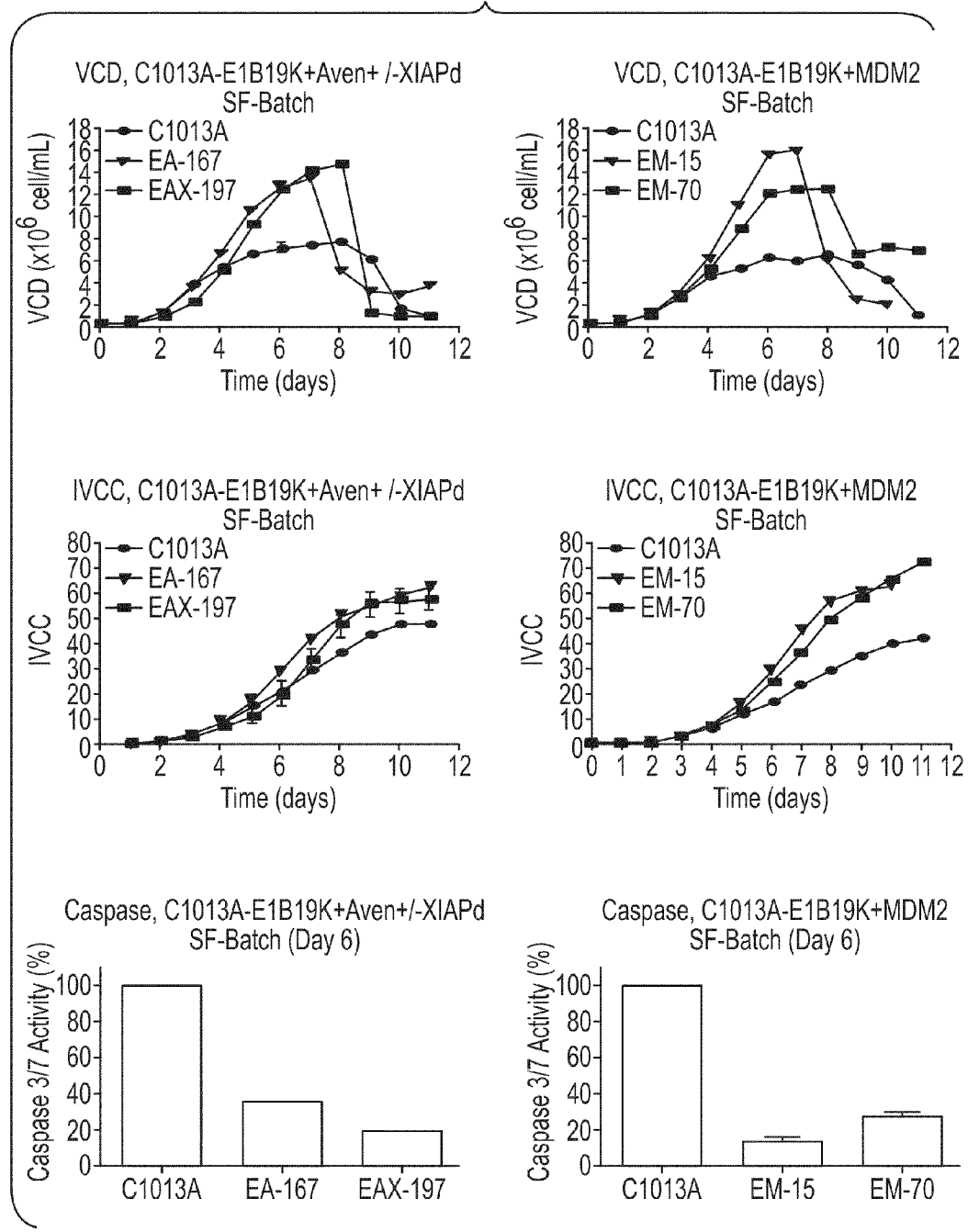
FIG. 3. Growth Profiles of cell lines generated from co-transfection of E1B19K and MDM-2. A) Viable Cell Density; B) Integrated Viable Cell Density; C) Down-regulation of Caspase 3/7

Growth profiles of EM-15 and EM-70 expressing E1B19K and MDM2 are shown in FIG. 3. For comparison, in a separate experiment, cell lines expressing E1B19K and AVEN (EA-167), or expressing E1B19K, AVEN and XIAPΔ (EAX-197) as well as the transfection host cell line, C1013A were included. The peak viable cell density (VCD) of control cell line reached 6×10e6 cells/ml whereas those of EM clones reached about 12×10e6 cells/ml to 16×10e6 cells/ml. The maximum VCD for EA-167 and EAX-197 was 13.6-13.9×10e6 cells/ml. The EM clones had higher IVCC compared to EA-167 or EAX-197. EM-70 had a 100% increase in IVCC over control as compared to 23% increase over control for EA-167. This data, along with the fact that cell lines expressing E1B19K alone were not sufficient for achieving the high IVCC observed in this experiment (Nivitchanyong et al., Biotechnol Bioeng 98:825-841 (2007)) suggests that MDM2 contributed to the increase in IVCC observed in EM-15 and EM-70 cell lines. Co-transfection of E1B19K, MDM2 and XIAPΔ failed to generate cell lines with higher VCD or IVCC as compared to (data not shown). Caspase 3/7 activity in EM-15 and EM-70 cell lines were 13% and 30%, respectively, from the control C1013A. For comparison, EA-167 and EAX-197 had 37% and 20% of caspase 3/7 activity as that of C1013A control. Apoptosis was also confirmed by FLOW as described above. 91% of control cells were positive for caspase 3/7 whereas 1-30% of cells within cell lines expressing apoptototic$^R$ genes were caspase 3/7 positive. Cell lines with the lowest caspase 3/7 activity (eg. B-31) did not necessarily have the highest IVCC.

Example 4

Cloning and Expression of Mutant MDM2

The vector expressing wild-type human MDM2 full-length cDNA (Genbank Accession M92424.1) was obtained from John Hopkins University. The MDM2$^{D300A}$ expression vector was generated by in vitro mutagenesis with a mutagenesis primer 5' gctgaagagggcttt gatgtgccggcttgt aaaaaaactatagtg 3' (SEQ ID NO: 15, resulting in a replacement of A at position 899 with C, and in substitution of Aspartic acid for Alanine in the predicted MDM2$^{D300A}$ protein. The mutagenesis was confirmed by sequencing. The MDM2$^{D300A}$ DNA sequence is shown in SEQ ID NO: 3 and the predicted MDM2$^{D300A}$ protein sequence is shown in SEQ ID NO: 4. This new mutant vector as well as its wild-type counterpart was used for transient and stable transfections.

The MDM2$^{D300A}$ and MDM2 wild type proteins were transiently expressed in Hek293 cells. Western blot demonstrated presence of higher levels of MDM2$^{D300A}$ in the cells when compared to the wild type MDM2, suggesting the mutant protein was more resistant to proteolytic degradation than the wild type MDM2.

Example 5

Generation of MDM2$^{D300A}$-Expressing Cell Lines

Stable cell lines over-expressing MDM2$^{D300A}$ or WT MDM2 proteins were generated as described in Example 1. Two host cell lines, C1013A and C1835A were used. The list of cell lines used in growth profile studies is shown in Table 2.

TABLE 2

| Cell line | Host | Transfected genes |
|---|---|---|
| A3 | C1013A | WT MDM2 |
| A4 | C1013A | WT MDM2 |
| B1 | C1013A | MDM2D300A |
| B5 | C1013A | MDM2D300A |
| C7 | C1835A | WT MDM2 |
| C8 | C1835A | WT MDM2 |
| D6 | C1835A | MDM2D300A |
| D7 | C1835A | MDM2D300A |
| | C1013A | Pool of wild-type MDM2 cells |
| | C1013A | Pool of MDM2A300D cells |
| | C1013A | none |
| | C1835A | none |
| EM70 | C1013A | E1B19K, MDM2 |
| C1013H | C1013A | Bcl2d |
| C1013J | C1013A | Bcl-XL |
| C1013K | C1013A | E1B19K, Aven, XIAPd |
| BMX13 | C1013A | Bcl-2d, MDM2, XIAPd |

Example 6

Effect of MDM2 on Longevity and Viability of CHOK1 Host Cell Lines

Figure 4A:
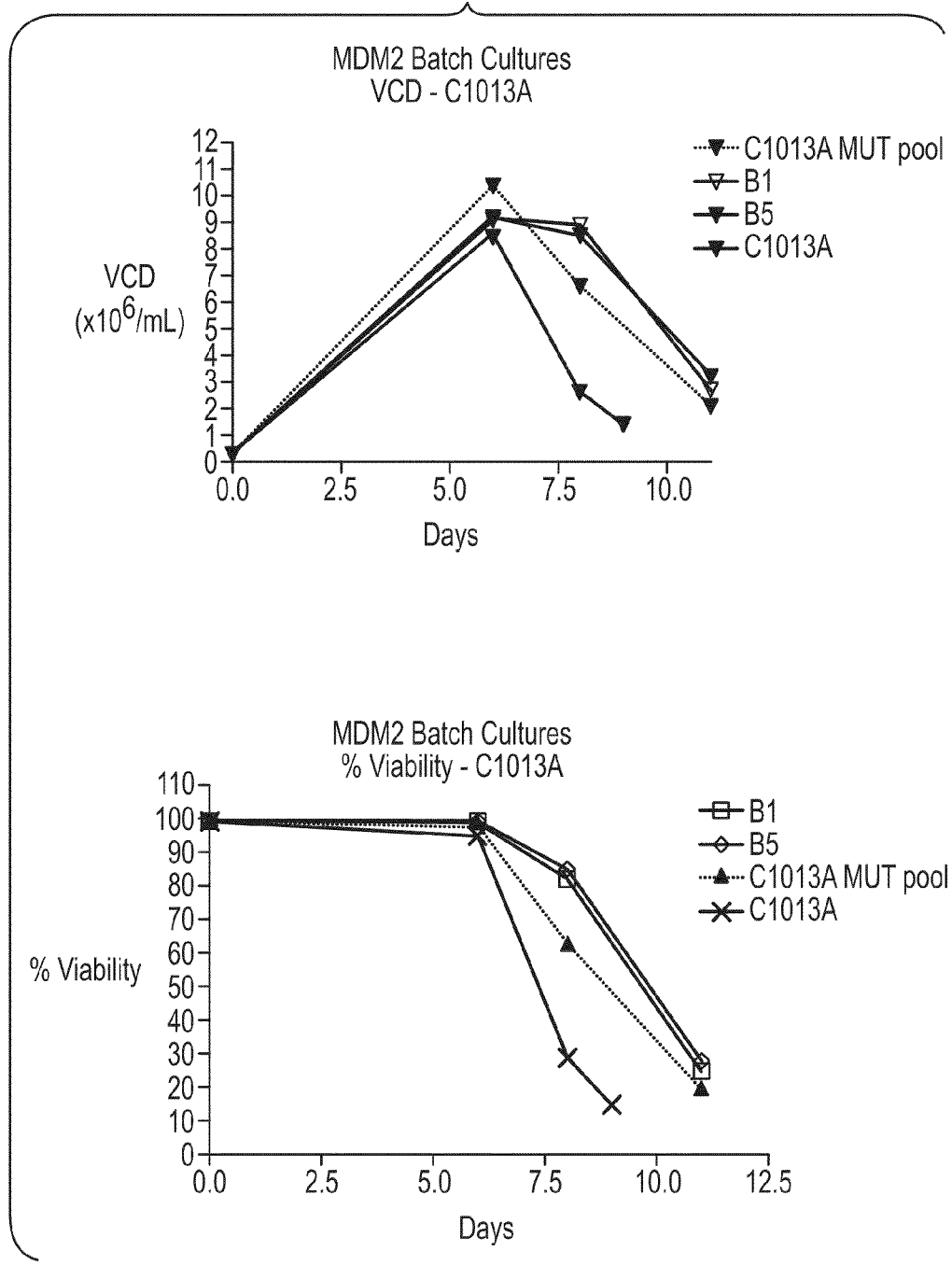
FIG. 4. Growth profiles of cell lines transfected with MDM2$^{D300A}$ in shake flask batch culture.
A. Transfected host was 1013A
B. Transfected host was C1835A FIG. 5. Growth profiles of 1013A cell line transfected with DM2$^{D300A}$ in shake flask fed-batch culture. A) Viable cell density; B) % viability.
Figure 4B:
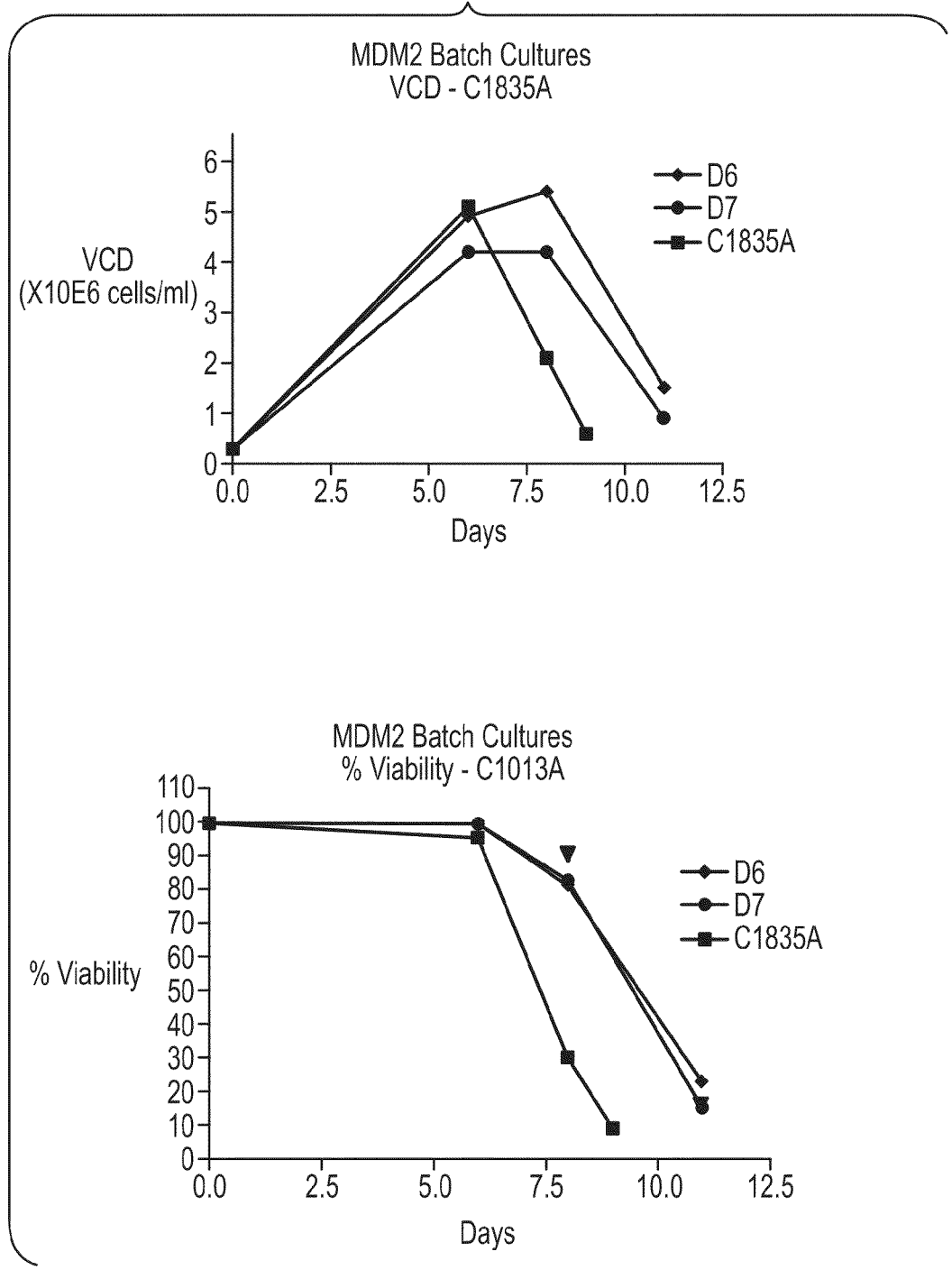
Figure 5A:
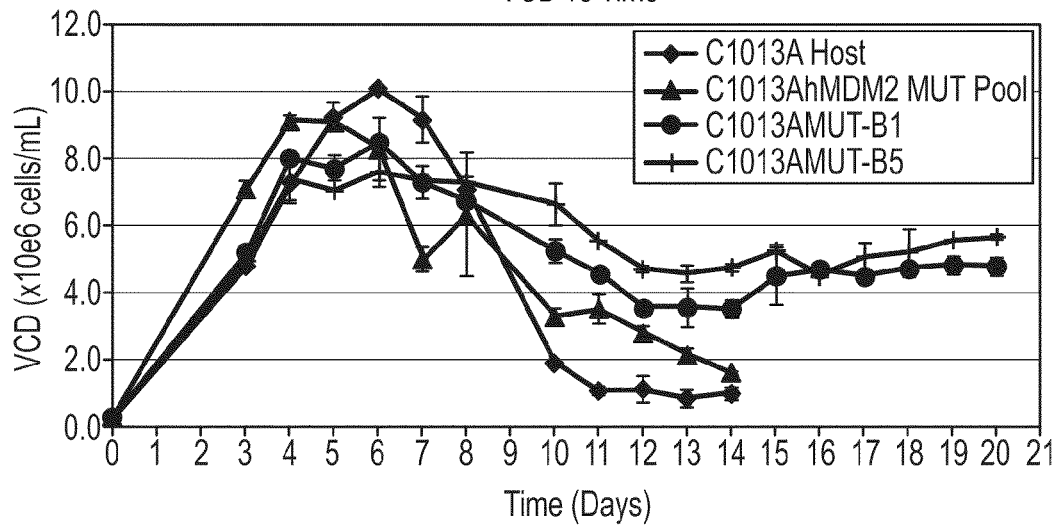
Figure 5B:
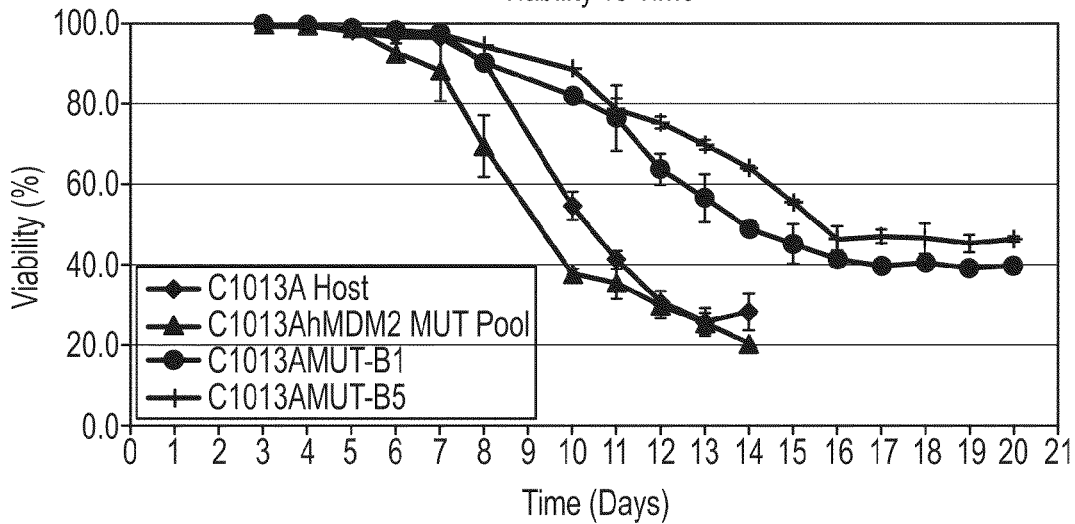

The growth profiles and viability (Shake-Flask/Batch) of C1013A-derived and C1835A-derived cell lines D6, B1 and B5 expressing the MDM2D300A gene are shown in FIG. 4. Using Centocor proprietary protein-free medium, the peak viable cell density (VCD) of C1013A control cell line was $8 \times 10^6$ cells/ml, and that of the C1835A control cell line was $5 \times 10^6$ cells/mL. Cell lines over-expressing MDM2$^{D300A}$ had increased longevity as compared to the control cell lines. In fed-batch cultures, B1 and B5 cell lines were maintained in culture for up to 20 days, whereas the untransfected host cell as well as the cells derived from bulk selected pool following transfection with MDM2$^{D300A}$ lost viability by day 14 of the culture (FIG. 5).

Example 7

Stability of the CHO Cell Lines Over-Expressing MDM2

The C1013A-derived and C1835A-derived CHO cell lines D6 and B5 over-expressing MDM2D300A were subjected to a 15-passage stability study, with and without the selection agent, geniticin. A growth curve study was conducted at the beginning and the end of the stability study for each cell line and peak viable cell density (indicative of cell line stability) was noted. The cultures without geneticin selection and at higher passages had equivalent or higher VCD's and thus can be considered to very stable in the absence of the selection reagent (Table 3).

TABLE 3

Peak VCD of Cell Lines Over-expressing MDM2.m (15-passage Stability Study)

| | Peak VCD ($10^6$/mL) |
|---|---|
| MUT-B5 (−) geneticin (p1) | 6.7 |
| MUT-B5 (+) geneticin (p1) | 6.4 |
| MUT-B5 (−) geneticin (p15) | 9.1 |
| MUT-B5 (+) geneticin (p15) | 7.3 |
| MUT-D6 (−) geneticin (p1) | 4.6 |
| MUT-D6 (+) geneticin (p1) | 4.5 |
| MUT-D6 (−) geneticin (p15) | 4.6 |
| MUT-D6 (+) geneticin (p15) | 5.4 |

Example 8

Productivity Studies Using MDM2 Over-Expressing Host Cell Lines

The cell line, A4, over-expressing MDM2 and B1, over-expressing MDM2$^{D300A}$ were transfected with a recombinant antibody heavy and light chain expression vector. The transfection mixture was first bulk selected using glutamine-free media containing Glutamine Synthetase supplements and 25 µM MSX. Subsequently, the mixture was plated in methocult for isolation of individual clones. About 100 resulting transfectomas per transfection were expanded into 24-well plate and a 14-day spent titer was measured by nephelometry. The average titers for the MDM2 and MDM2D300A cell lines expressing CNTO328 were 90 mg/L, and significantly higher than that of clones derived from C1013A, which was 21.3 mg/L.

Figure 6:
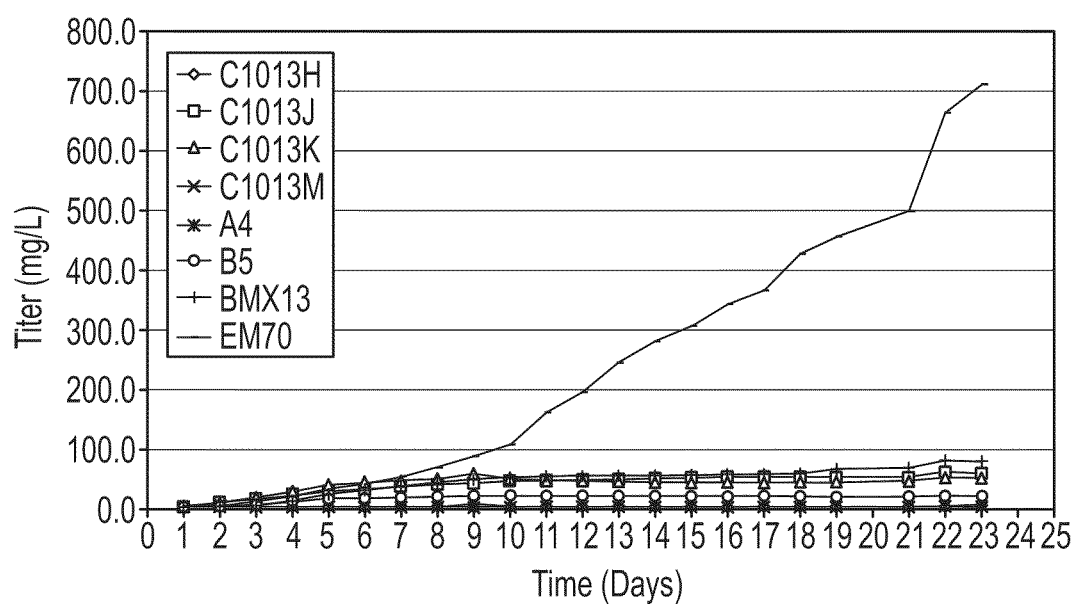
FIG. 6. Antibody titers during fed batch CHO culture.

In a separate experiment, CHOK1SV cells were transfected with MDM2 and E1B19K and one clone, EM70 stably expressing E1B19K and MDM2 was transfected with a recombinant heavy and light chain antibody expression vector (Dorai et al., Biotechnol. Bioeng., 103:592-608 (2009). The transfection mixture was first bulk selected using glutamine-free media containing Glutamine Synthetase supplements and 25 uM MSX. For comparison, several other cell lines including C1013A (control), C1013M, C1013J, C1013K, A4, B5, BMX13. Following bulk selection for 29 days, the surviving cells were subjected to a shake-flask fed-batch study. EM70 provided antibody titers of >700 mg/L on d23 whereas the titers of the remaining cell lines did not exceed 100 mg/L (FIG. 6). An exponential culture of CHOK1SV was transfeced with vectors expressing E1B19K and MDM2. Two days later antibiotic selection protocol was initiated. By day 29, all untransfected cells were eliminated whereas the antibiotic resistant cells (transfected pool) had survived.

These cells were used for performing a shake-flask fed-batch growth profile study. 2e5 cells/ml was seeded in Mach-1 medium containing supplements. Starting day-2, the cultures were fed daily a nutrient mix of glucose and amino acids. Cell counts and titer was measured daily.

The present invention now being fully described, it will be apparent to one of ordinary skill in the art that many changes and modifications can be made thereto without departing from the spirit or scope of the appended claims.

The invention claimed is:

1. A method of producing a secreted protein in a Chinese Hamster Ovary (CHO) fed batch cell culture, comprising culturing a CHO cell line over-expressing MDM2 and E1B19K and one or more genes encoding the secreted protein, wherein the titer of the produced secreted protein is at least 600 mg/L at day 23 of the fed batch culture.

2. The method of claim 1 wherein the CHO cell line is CHO-K1.

3. The method of claim 1 wherein the CHO cell line is CHO-K1SV.

4. The method of claim 1 wherein the secreted protein is an antibody heavy chain and an antibody light chain.

* * * * *